(12) United States Patent
Connelly et al.

(10) Patent No.: US 8,507,212 B2
(45) Date of Patent: *Aug. 13, 2013

(54) PROCESS FOR IN VIVO TREATMENT OF SPECIFIC BIOLOGICAL TARGETS IN BODILY FLUIDS

(75) Inventors: Patrick R. Connelly, Rochester, NY (US); Jeffrey L. Helfer, Webster, NY (US); Andrew W. Custer, Davis, CA (US); Michael B. Kim, Boston, MA (US)

(73) Assignee: Biomed Solutions LLC, West Henrietta, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/346,932

(22) Filed: Jan. 10, 2012

(65) Prior Publication Data

US 2012/0179143 A1 Jul. 12, 2012

Related U.S. Application Data

(60) Continuation of application No. 12/219,139, filed on Jul. 16, 2008, now Pat. No. 8,105,793, which is a division of application No. 10/787,279, filed on Feb. 26, 2004, now abandoned, and a continuation of application No. 10/208,288, filed on Jul. 30, 2002, now abandoned, and a continuation-in-part of application No. 10/131,361, filed on Apr. 24, 2002, now Pat. No. 7,244,232, and a continuation-in-part of application No. 09/918,078, filed on Jul. 30, 2001, now Pat. No. 6,743,190, and a continuation-in-part of application No. 09/918,076, filed on Jul. 30, 2001, now Pat. No. 6,793,642, and a continuation-in-part of application No. 09/852,876, filed on May 10, 2001, now abandoned, and a continuation-in-part of application No. 09/850,250, filed on May 7, 2001, now Pat. No. 6,488,704, which is a continuation-in-part of application No. 09/800,823, filed on Mar. 7, 2001, now Pat. No. 6,750,055.

(60) Provisional application No. 60/450,450, filed on Feb. 26, 2003, provisional application No. 60/308,628, filed on Jul. 30, 2001.

(51) Int. Cl.
*G01N 33/53* (2006.01)

(52) U.S. Cl.
USPC ....... 435/7.2; 435/7.21; 435/7.23; 435/288.5; 436/518; 436/519; 436/524; 436/525; 436/527; 436/528; 436/531

(58) Field of Classification Search
None
See application file for complete search history.

(56) References Cited

U.S. PATENT DOCUMENTS

| 4,284,553 A | 8/1981 | Brown |
| 4,352,883 A | 10/1982 | Lim |

(Continued)

FOREIGN PATENT DOCUMENTS

| EP | 0809523 B1 | 7/1999 |
| EP | 1101457 A2 | 5/2001 |

(Continued)

*Primary Examiner* — Chris L Chin
(74) *Attorney, Agent, or Firm* — Hiscock & Barclay, LLP

(57) ABSTRACT

A process for treating biological targets in a fluid of a biological organism, including introducing a fluid comprising a biological target to an assembly comprising an inlet connected to receive the fluid and an outlet connected to pass the fluid from the assembly, wherein the assembly comprises a flow chamber for conveying a flow of the fluid, and a capture zone comprising a target-specific binding agent, wherein during flow of the fluid through the flow chamber, the biological target undergoes flux rolling along the target-specific binding agent.

16 Claims, 18 Drawing Sheets

(56) References Cited

U.S. PATENT DOCUMENTS

| | | |
|---|---|---|
| 4,392,909 A | 7/1983 | Bohn |
| 4,409,331 A | 10/1983 | Lim |
| 4,559,039 A | 12/1985 | Ash |
| 4,647,536 A | 3/1987 | Mosbach |
| 4,663,286 A | 5/1987 | Tsang |
| 4,673,566 A | 6/1987 | Goosen |
| 4,714,680 A | 12/1987 | Civin |
| 4,798,786 A | 1/1989 | Tice |
| 4,902,295 A | 2/1990 | Walthall |
| 4,971,833 A | 11/1990 | Larsson |
| 4,980,299 A | 12/1990 | Batz |
| 4,997,443 A | 3/1991 | Walthall |
| 5,053,332 A | 10/1991 | Cook |
| 5,133,363 A | 7/1992 | Guirguis |
| 5,192,537 A | 3/1993 | Osband |
| 5,227,298 A | 7/1993 | Weber |
| 5,308,626 A | 5/1994 | Landucci |
| 5,324,518 A | 6/1994 | Orth |
| 5,399,501 A | 3/1995 | Pope |
| 5,399,580 A | 3/1995 | Daluge |
| 5,484,596 A | 1/1996 | Hanna |
| 5,643,569 A | 7/1997 | Jain |
| 5,686,281 A | 11/1997 | Roberts |
| 5,755,775 A | 5/1998 | Trerotola |
| 5,788,963 A | 8/1998 | Murphy |
| 5,976,780 A | 11/1999 | Shah |
| 5,980,889 A | 11/1999 | Butler |
| 6,099,730 A | 8/2000 | Ameer |
| 6,165,225 A | 12/2000 | Antanavich |
| 6,177,542 B1 | 1/2001 | Ruoslahti |
| 6,207,144 B1 | 3/2001 | Kurth |
| 6,221,315 B1 | 4/2001 | Giesler |
| 6,231,600 B1 | 5/2001 | Zhong |
| 6,265,229 B1 | 7/2001 | Fodstad |
| 6,274,342 B1 | 8/2001 | Gutierrez-Ramos |
| 6,306,575 B1 | 10/2001 | Thomas |
| 6,320,023 B1 | 11/2001 | Godiska |
| 6,365,418 B1 | 4/2002 | Wagner |
| 6,399,063 B1 | 6/2002 | Hudziak |
| 6,419,917 B1 | 7/2002 | Li |
| 6,458,349 B1 | 10/2002 | Li |
| 6,521,211 B1 | 2/2003 | Unger |
| 7,006,858 B2 | 2/2006 | Silver |
| 2001/0000802 A1 | 5/2001 | Soykan |
| 2001/0001817 A1 | 5/2001 | Humes |
| 2001/0010022 A1 | 7/2001 | Dauner |
| 2001/0044655 A1 | 11/2001 | Patnaik |
| 2001/0051834 A1 | 12/2001 | Frondoza |
| 2002/0022860 A1 | 2/2002 | Borillo |
| 2002/0032414 A1 | 3/2002 | Ragheb |
| 2003/0113478 A1 | 6/2003 | Dang |

FOREIGN PATENT DOCUMENTS

| | | |
|---|---|---|
| EP | 1174156 A2 | 1/2002 |
| WO | 95/04521 | 2/1995 |
| WO | 98/16238 | 4/1998 |
| WO | 99/37751 | 7/1999 |
| WO | 99/44583 | 9/1999 |
| WO | 00/68689 | 11/2000 |
| WO | 01/62895 | 8/2001 |
| WO | 01/66698 | 9/2001 |
| WO | 02/20825 | 3/2002 |
| WO | 02/009650 | 7/2002 |

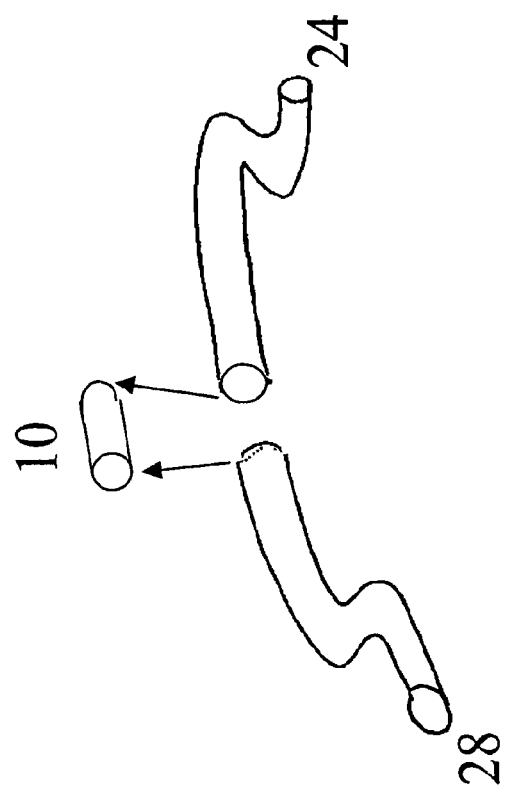

PROCESS FOR IN VIVO TREATMENT OF SPECIFIC BIOLOGICAL TARGETS IN BODILY FLUIDS

CROSS-REFERENCE TO RELATED APPLICATIONS

This application is a continuation of co-pending application Ser. No. 12/219,139, filed Jul. 16, 2008, which is a divisional of application Ser. No. 10/787,279 filed Feb. 26, 2004 (now abandoned), the contents of both of which are herein incorporated by reference, and which claims priority of provisional application No. 60/450,450 filed Feb. 26, 2003, and which claims priority based on application Ser. No. 10/208,288, filed Jul. 30, 2002 (now abandoned), which is a continuation-in-part of application Ser. No. 09/800,823, filed Mar. 7, 2001 (now U.S. Pat. No. 6,750,055), application Ser. No. 09/850,250, filed May 7, 2001 (now U.S. Pat. No. 6,488,704), application Ser. No. 09/918,076, filed Jul. 30, 2001 (now U.S. Pat. No. 6,793,642), application Ser. No. 09/918,078, filed Jul. 30, 2001 (now U.S. Pat. No. 6,743,190), and application Ser. No. 10/131,361 (now U.S. Pat. No. 7,244,232), filed Apr. 24, 2002, which claims the benefit of provisional application No. 60/308,628, filed Jul. 30, 2001; priority is also claimed from applicants' application Ser. No. 10/131,361, filed Apr. 24, 2002 (now U.S. Pat. No. 7,244,232), which is a continuation-in-part of application Ser. No. 09/800,823 (now U.S. Pat. No. 6,750,055), filed Mar. 7, 2001, application Ser. No. 09/850,250 (now U.S. Pat. No. 6,488,704), filed May 7, 2001, application Ser. No. 09/852,876, filed May 10, 2001 (now abandoned), application Ser. No. 09/918,076, filed Jul. 30, 2001 (now U.S. Pat. No. 6,793,642), application Ser. No. 09/918,078, (now U.S. Pat. No. 6,743,190) filed Jul. 30, 2001, which claims the benefit of provisional application No. 60/308,628, filed Jul. 30, 2001.

FIELD OF THE INVENTION

A process for the in vivo treatment of the bodily fluid of a biological organism wherein said organism is implanted with a device, the bodily fluid is brought into contact with a binding agent within the device and the velocity of at least one of the cellular components of the fluid is reduced.

BACKGROUND

The prior art describes numerous processes detailing the isolation of desired biological targets from bodily fluids. As discussed in the prior art, a biological entity of interest typically is derived from a sample that is removed from a donor, which sample contains a heterogeneous mixture of cells and other biological substances. These substances span a size scale from the macroscopic to the molecular. The heterogeneous sample is subjected to one or more separation and purification procedures in order to obtain a preparation that is enriched with the biological target. Typical heterogeneous samples from which a biological target may be derived include: peripheral whole blood, bone marrow, tumor tissue, sputum, lymphatic fluid, ascites fluid, pleural fluid, spinal fluid, urine, gastro-intestinal fluid, bile, umbilical cord blood, amniotic fluid and so forth. Often, the amount of the biological entity of interest in the sample is negligible. Therefore, the target cell, stem cells, metastatic cancer cells, viruses, prion, and so forth, must be separated and purified from an overwhelming number of very similar, often nearly identical, non-target biological entities and other unwanted biological substances. Methods for separating and purifying cells and other biological entities have been developed. So-called positive separation methods take advantage of immunoaffinity-based technology. In an immunoaffinity-based method, antibody specific for a biological entity, for example a cell-type of interest, is linked to the surface of a solid such as a particle or filtration membrane. The captured cells, that is, cells bound to the solid through bonding to the antibody, are then separated from non-bound cells by filtration, adsorption on a column, partitioning in a magnetic field, centrifugation, and so on.

International application WO09944583 describes an implantable porous device used for isolating and/or stimulating the immune response within an individual that can also be used to sequester immune cells, which can later be introduced to the body. A primary embodiment of this invention is the implantation of a porous/permeable structure contained within an impermeable structure. The porous structure contains an antigen to initiate a humoral immune response. Diseased immune cells can also be sequestered within the device and caused to undergo apoptosis via specific cytokine initiation (p. 12, line 20). Immune cells may then be captured within the porous membrane, the device extracted and the cells later introduced within the body. It is disclosed that immune cells can be isolated and later used for various immunotherapy treatments (p. 13-14).

A continuous-flow immunoaffinity method for separating target cells from non-target cells in whole blood withdrawn from a donor is described in U.S. Pat. No. 6,221,315. In this method target cells bind to dense, target cell specific particles that are then centrifuged and, thereby, the target cells are separated from non-bound cells.

A method for isolating metastatic cancer cells from donated blood is described in PCT Publication WO 0220825.

A capillary apparatus and associated immunoaffinity method for separating target cells from cells in a mixture is described in PCT Publication WO 0068689.

In PCT Publication WO 0162895, methods for concentrating and expanding T-cells are described, which methods depend upon binding of T-cells to co-stimulatory ligands attached to a surface. T-cells are derived from circulating blood obtained from an individual by apheresis or leukapheresis. In one embodiment of the disclosed methods, paramagnetic particles having attached ligands specific for the target cell surface moiety that induces cell stimulation are introduced into an animal. As stated in the PCT Publication, a magnetic field may be applied to a discrete region of the animal to induce localization and stimulation of the target cells bound to the particles at the discrete region.

Stem cells are cells capable of both indefinite proliferation and differentiation into specialized cells that serve as a continuous source for new cells for such tissues as blood, myocardium, liver, etc. Hematopoietic cells are rare, pluripotent cells, having the capacity to give rise to all lineages of blood cells. Stem cells undergo a transformation into progenitor cells, which are the precursors of several different blood cell types, including erythroblasts, myeloblasts, monocytes and macrophages. Stem cells have a wide range of potential applications, particularly in the autologous treatment of cancer patients.

Typically, stem cell products (true stem cells, progenitor cells and CD34+ cells) are harvested from bone marrow of a donor in a procedure, which may be a painful, and requires hospitalization and general anesthesia. More recently, methods have been developed enabling stem cells and committed progenitor cells to be obtained from donated peripheral blood or peripheral blood collected during a surgical procedure.

Progenitor cells, whether from bone marrow or peripheral blood, can be used to enhance the healing of damaged tissues, such as myocardium damaged by myocardial infarction, as well as enhance hematologic recovery following an immunosuppressive procedure such as chemotherapy.

A number of immunotherapy strategies for treating cancer patients have been under development. These include (1) adoptive immunotherapy using different types of stimulated autologous cells, (2) systemic transfer of allogeneic lymphocytes, (3) vaccination at a distant site to generate a systemic tumor-specific immune response, and (4) implantation of immune cells directly into a tumor.

In adoptive immunotherapy, cells isolated from peripheral blood withdrawn from a patient are stimulated and then returned to the same patient; thus, the cells are histocompatible. The autologous lymphocytes may be stimulated ex-vivo with tumor-associated antigen to make them tumor-specific (Zarling et al. (1978) Nature 274:269-71 and U.S. Pat. No. 5,192,537) or autologous lymphocytes and killer cells can be stimulated non-specifically as described in U.S. Pat. No. 5,308,626. The entire disclosure of each of these United States patents is hereby incorporated by reference into this specification.

Peripheral blood-derived lymphocytes cultured in the presence of interleukin-2 form lymphokine-activated killer (LAK) cells, which have been used to treat individuals suffering from metastatic melanoma and renal cell carcinoma (Rosenberg (1987) New Engl. J. Med. 316:889-897). LAK cells have also been used to treat brain tumors (Merchant et al. (1988) Cancer 62:665-671 and (1990) J. Neuro. Oncol. 8:173-198).

Another form of adoptive immunotherapy involves the use of autologous tumor-infiltrating lymphocytes (TIL) (Rosenberg et al. (1990) New Engl. J. Med. 323:570-578). Unfortunately, a clinically useful quantity of TILs from a donor can only be obtained and prepared in a limited number of tumor types.

In adoptive transfer of allogeneic lymphocytes, lymphocytes obtained from a donor are used to induce a general level of immune stimulation against tumors (Strausser et al. (1981) J. Immunol. Vol. 127, No. 1, Zarling et al. (1978) Nature 274:269-71 and Kondo et al. (1984) Med Hypotheses 15:241-77).

The third immunotherapy strategy listed above, involves generating an active systemic tumor-specific immune response of host origin by administering a vaccine composition (tumor-antigen vaccines and anti-idiotype vaccines) at a site distant from the tumor.

Another approach involves using tumor cells derived from a donor to be treated (Schirrmacher et al. (1995) J. Cancer Res. Clin. Oncol. 121:487-489 and U.S. Pat. No. 5,484,596).

Autologous tumor cells have been used in combination with allogeneic cytokine-secreting cells in treating cancers, as described in PCT Publication WO 98/16238.

The fourth immunotherapy strategy listed above, intratumor implantation, involves delivering effector cells in proximity to a tumor site. Different effector-cell types (syngeneic lymphocytes, non-adherent LAK cells, adherent LAK cells, syngeneic cytotoxic T lymphocytes (CTL) raised against tumor antigens, and allogeneic CTL raised against alloantigens) have shown success in a rat gliosarcoma cell line (Kruse et al. (1990) Proc. Natl. Sci. USA, 87:9377-9381).

The T-cell antigen receptor (TCR) is a multisubunit immune recognition receptor that associates with the CD3 complex and binds to peptides presented by the major histocompatibility complex (MHC) class I and II proteins on the surface of antigen-presenting cells (APCs). Binding of TCR to the antigenic peptide on the APC is the central event in T-cell activation. A requirement for MHC-matched APCs as accessory cells for T-cell stimulation is problematic because APCs are relatively short-lived and, therefore, in a long-term culture system they must be continually obtained from a donor and replenished.

The isolation and use of dendritic cells from donated human peripheral blood in immunotherapy methods for treating prostate cancer is described in U.S. Pat. No. 5,788,963.

The use of hematopoietic and cardiac stem cells for regenerating damaged myocardium is described in PCT Publication WO 209650.

The use of human umbilical blood as a source of neural cells for transplantation is described in PCT Publication WO 0166698.

Clearly, a need exists for providing many different endogenous cell-types, infected or uninfected, from human and non-human donors for use in numerous and varied human and veterinary research, diagnostic and therapeutic applications. Endogenous cells from a donor, in general, may be used for genetic screening purposes in birth disorders or in organ replacement therapy.

A need exists for capturing circulating cells, such as cancer cells with the potential to metastasize, viruses, bacteria, prions and other biological entities. This need encompasses research, diagnostics and therapeutics applications in diverse disciplines including, genetics, hematology, microcirculation, oncology, infectious disease, immunology and microbiology.

There exists a need for obtaining cellular samples from donors that are enriched in the desired biological target. Because a heterogeneous sample contains a negligible amount of a biological entity of interest, the limits of separation methods to provide viable and potent biological target in sufficient purity and amount for research, diagnostic or therapeutic use are often exceeded. Because of the low yield after separation and purification, some cell-types, such as stem cells, progenitor cells and immune cells (particularly T-cells) must be placed in long-term culture systems under conditions that enable cell viability and clinical potency to be maintained and under which cells can propagate (cell expansion). Such conditions are not always known. In order to obtain a sufficient amount of a biological target, a large amount of a sample, such as peripheral blood, must be obtained from a donor at one time, or samples must be withdrawn multiple times from a donor and then subjected to one or more lengthy, expensive, and often low-yield separation procedures to obtain a useful preparation of the biological target. Taken together, these problems place significant burdens on donors, separation methods, laboratory personnel, clinicians and patients. These burdens significantly add to the time and costs required to isolate the desired cells.

There exists a need for obtaining cells from non-humans, which cells comprise particular antigens or antibodies of interest. The transcription and translation levels of any number of constituents, mechanical properties, in vitro memory properties or genetic properties of cells can be analyzed. Capturing immune cells, stem cells and committed progenitor cells, and metastatic cancer cells, blood borne viruses are of particular interest.

There exists a need for devitalizing circulating cells to minimize their potential to induce or promote disease in the host.

It is an object of this invention to provide a sample directly from a donor, which sample is enriched or sufficiently enriched with biological target.

It is an object of this invention to provide an implantable target specific capture device that enables easy and repeated access in order to obtain samples when desired, without requiring removal of the device from a donor, which samples are enriched with the target of interest.

It is an object of this invention to provide a capture device that could be configured to simultaneously capture multiple targets (e.g. multiple types of metastatic cancer cells).

It is an object of this invention to provide a capture device that could be easily modified to enable it to capture different types of cells.

It is an object of this invention to provide a capture device that could capture, sequester, and maintain the viability of the captured cells until the cells are harvested.

It is an object of this invention to provide a capture device that could devitalize (i.e. destroy) the captured cells, such as metastatic cancer cells or HIV-infected cells, particularly without the need for additional interactions from the host.

These and other objects afforded by the methods and implantable target specific capture devices of the invention will become evident upon consideration of the following drawings, summary and detailed description.

SUMMARY OF THE INVENTION

In accordance with one embodiment of the invention, there is provided a process for treating biological targets within the fluid of an organism comprising the steps of (1) feeding the fluid into a chamber which is comprised of a target specific binding agent, (2) modifying the flow dynamics of the fluid, and (3) allowing the biological target to bind with the target specific binding agent.

DEFINITION OF TERMS

As described herein, several terms are given specific meaning within the context of this writing. These terms are hereby defined as follows:

As described herein, the term "in-vivo device" refers to a device that attaches to fluid flow systems within the body, such as a vein or an artery. Portions of the device may be located outside the body and connected to the internal flow system by connections through the skin.

The term "biological target" refers to any endogenous infected or uninfected cell, or similar biological particles, including metastatic cancer cells and HIV infected cells, or virus, or bacterium, or prion, or other biological entity of interest that may be present in a fluid of a human or non-human donor. Endogenous cells include but are not limited to, subsets of cells within a defined cell family, for example a B-lymphocyte or a T-lymphocyte in the lymphocyte family, or a cytolytic T-lymphocyte in the T-lymphocyte family, or an entire family of cells, such as the lymphocyte family. Examples of other endogenous cells are fibroblasts, neuroblasts, hematopoietic stem cells, hematopoietic progenitor cells (CD34+ cells), mesenchymal stem cells, dendritic cells, cytolytic T-cells (CD8+ cells), other leukocyte populations, pluripotent stem cells, multi-potent stem cells, embryonic cells or islet cells. Biological targets include populations of cells having distinct phenotypic characteristics: B-cells, T-cells, NK cells, other blood cells, neuronal cells, glandular (endocrine) cells, bone forming cells (osteoclasts, etc.), germ cells (e.g., oocytes), epithelial cells lining reproductive organs, trophoblastic and placental cells in amniotic fluid and mesenchymal progenitor, neuronal progenitor, neuroectodermal cells. A biological target such as a leukocyte, stem cell or an insoluble protein may be in suspension within a fluid of a donor or it may be dispersed as a microscopic colloid, such as a large soluble protein or it may be in true molecular solution, such as a small molecule.

The term "target specific binding agent" refers to a molecule or fragment of a molecule that binds to a particular biological target. A target specific binding agent may bind a cell surface moiety, such as a receptor, an antigenic determinant, an integrin, a cell adhesion molecule, or other moiety present on a cell-type of interest. A binding agent may be specific for a region of a protein, such as a prion, a capsid protein of a virus or some other viral protein, and so on. A target specific binding agent may be a protein, peptide, antibody, antibody fragment, a fusion protein, synthetic molecule, an organic molecule (e.g., a small molecule), or the like. In general, a target specific binding agent and its biological target refer to a ligand/anti-ligand pair. Accordingly, these molecules should be viewed as a complementary/anti-complementary set of molecules that demonstrate specific binding, generally of relatively high affinity Cell surface moiety-ligand pairs include, but are not limited to, T-cell antigen receptor (TCR) and anti-CD3 mono or polyclonal antibody, TCR and major histocompatibility complex (MHC)+antigen, TCR and super antigens (for example, staphylococcal enterotoxin B (SEB), toxic shock syndrome toxin (TSST), etc.), B-cell antigen receptor (BCR) and anti-immunoglobulin, BCR and LPS, BCR and specific antigens (univalent or polyvalent), NK receptor and anti-NK receptor antibodies, FAS (CD95) receptor and FAS ligand, FAS receptor and anti-FAS antibodies, CD54 and anti-CD54 antibodies, CD2 and anti-CD2 antibodies, CD2 and LFA-3 (lymphocyte function related antigen-3), cytokine receptors and their respective cytokines, cytokine receptors and anti-cytokine receptor antibodies, TNF-R (tumor necrosis factor-receptor) family members and antibodies directed against them, TNF-R family members and their respective ligands, adhesion/homing receptors and their ligands, adhesion/homing receptors and antibodies against them, oocyte or fertilized oocyte receptors and their ligands, oocyte or fertilized oocyte receptors and antibodies against them, receptors on the endometrial lining of uterus and their ligands, hormone receptors and their respective hormone, hormone receptors and antibodies directed against them, and others. Other examples may be found by reference to U.S. Pat. No. 6,265,229; U.S. Pat. No. 6,306,575 and WO 9937751.

The term "enriched" means that the amount of biological target contained in a unit volume of donor fluid from which it is derived is less than the amount contained after release from an implanted target specific capture device or multiple devices and reconstitution into an identical volume of suitable liquid medium. The term "sufficiently enriched" means there is a sufficient amount of biological target within an implanted device or multiple devices such that the biological target may be used directly in a research, diagnostic or therapeutic application for which it is intended, or there is a sufficient amount of biological target so as to significantly reduce the amount of sample required to obtain a useful preparation using conventional separation and purification methods such as those noted earlier.

The term "bio-active agent" includes, for example, cytokines or any substance that may either induce or reduce cell viability or potency. A bio-active agent may be a peptide, a nucleic acid, a protein, a small organic molecule, an anti-thrombogenic agent, an antibiotic, an antibacterial agent, an antiviral agent, a heparin, a prostaglandin, urokinase, streptokinase, a polysaccharide, a sulfated polysaccharide, an albumin, a pharmaceutical agent, a growth factor, an antibody, an adhesion factor, an integrin, or any combination, derivative or modification thereof.

The term "fluid communication" means that two objects A and B are related such that a pathway, conduit, channel or passageway exists between objects A and B enabling a volume element of fluid at a locus of A to flow, move, pass, be conducted or transported, along the pathway, conduit, channel or passageway to a locus b of object B. The pathway, conduit, channel or passageway may be linear, non-linear, convoluted, or be of any form as long as a volume element of fluid can pass from object A to object B.

The term "capture zone" refers to any region or locus of an implantable device that comprises target specific binding agent immobilized thereto or therein. If the construction of a capture zone is such that it forms a volume element, the volume element may comprise any natural or synthetic polymer, fiber, diatomaceous earth, glass, metal, colloid, or plastic, and so on, or any combination thereof that may or may not be biodegradable or that may be biodegradable in one embodiment and non-biodegradable in another embodiment or vice versa. The natural or synthetic polymer, fiber, diatomaceous earth, glass, metal, colloid, or plastic, and so on, may be integral with the material substance that forms the capture zone or it may not be integral with it. The natural or synthetic polymer, fiber, diatomaceous earth, glass, metal, colloid, or plastic, and so on, may be particulate, such as in the form of spherical or substantially spherical beads. It may be laminar, in the form of multiple sheets, corrugated, smooth, fibrous, fiber bundles, porous, or of uniform or non-uniform shape and size, or any combination thereof. Biological target specific binding agent, and/or bio-active agent may be immobilized directly to the material substance forming a capture zone or a material substance on a surface or within a volume element of the capture zone.

The term "immobilized", within the context of the present invention, means rigidly or substantially localized at a site, region or locus by way of covalent or non-covalent bonding or encapsulation. Numerous methods and materials for immobilizing molecules to substrates are well known to skilled artisans. For example, see: U.S. Pat. No. 4,980,299; U.S. Pat. No. 4,284,553; U.S. Pat. No. 6,365,418; U.S. Pat. No. 5,399,501 and U.S. patent application Ser. No. 2001 0044655. Encapsulation of biological substances is also well known to skilled artisans and is well documented. For example, see: U.S. Pat. No. 5,227,298; U.S. Pat. No. 5,053,332; U.S. Pat. No. 4,997,443; U.S. Pat. No. 4,971,833; U.S. Pat. No. 4,902,295; U.S. Pat. No. 4,798,786; U.S. Pat. No. 4,673,566; U.S. Pat. No. 4,647,536; U.S. Pat. No. 4,409,331; U.S. Pat. No. 4,392,909; U.S. Pat. No. 4,352,883; U.S. Pat. No. 4,663,286; and U.S. Pat. No. 5,643,569.

The term "chemical attractant" or "chemoattractant" means a substance capable of luring a biological target that is capable of migration to the capture zone. One or more chemical attractants may be included in a target specific capture device. Reference may be had, e.g., U.S. Pat. No. 6,419,917; U.S. Pat. No. 6,274,342; U.S. Pat. No. 6,458,349; U.S. Pat. No. 6,320,023; and U.S. Pat. No. 6,207,144.

The term "bio-compatible" means not toxic or not known to be toxic to a living being.

The term "implantable device" refers to any article that may be used within the context of the methods of the invention for changing the concentration of a cell of interest in vivo. An implantable biological target capture device may be, inter alia, a stent, catheter, cannula, capsule, patch, wire, infusion sleeve, fiber, shunt, graft, and so on. An implantable biological target specific capture device and each component part thereof may be of any bio-compatible material composition, geometric form or construction as long as it is capable of being used according to the methods of the invention. The literature is replete with publications that teach materials and methods for constructing implantable devices and methods for implanting such devices, including: U.S. Pat. No. 5,324,518; U.S. Pat. No. 5,976,780; U.S. Pat. No. 5,980,889; U.S. Pat. No. 6,165,225; U.S. Patent Publication 2001 0000802; U.S. Patent Publication 2001 0001817; U.S. Patent Publication 2001 0010022; U.S. Patent Publication 2001 0044655; U.S. Patent Publication 2001 0051834; U.S. Patent Publication 2002 0022860; U.S. Patent Publication 2002 0032414; EP 0809523; EP 1174156; EP 1101457; WO 9504521.

The term "anti-thrombogenic" or "anticoagulant" means the ability to counteract the tendency for an organism's blood to clot or coagulate, called thrombosis.

The term "devitalizing" refers to the ability of a substance to kill or incapacitate a cell such that it is no longer capable of acting in a functional capacity. A "devitalized" cell is unable to function in the same manner it did before devitalization. For example, a metastatic cancer cell could be devitalized not only by killing the cell via lysis, necrosis, or programmed cell death, but could be made to be no longer able to divide. Similarly, an immune cell, such as an activated T cell, may not only be killed via lysis, necrosis, or programmed cell death, but may be forced to no longer be activated.

The term "activating" refers to the ability of a bio-active agent to impart additional functionality to a biological target. The functionality is not expressed by the biological target until after it has been acted upon by the bio-active agent. By way of illustration, T cells may be activated.

The term "differentiate" refers to the process of causing one cell type to change into another cell type. For example, a stem cell may differentiate into a specialized cell type.

The term "morphological characteristic" refers to the properties of a biological target that gives rise to its function. For example, changing the morphological characteristics of a biological target means to change its properties such that it is devitalized, activated, or differentiated.

"Cell holding binding" means binding of a biological target such that the target is no longer able to leave a capture zone. The duration of the binding may be temporary or it may be permanent.

The term "margination" refers to the migration of a biological target from a position in its carrier fluid to the wall of the channel that carries the fluid. The concentration of marginated biological targets will be enriched near the walls of the channel. An agent is deemed to be margined when its translational velocity is below the critical hydrodynamic velocity ($V_{crit}$) at a radial position one cell radius from the channel wall. The critical hydrodynamic velocity for a given tube may be calculated from the Navier-Stokes equation: $V_{crit}=(2Q/D_2)\epsilon(2-\epsilon)$ where $\epsilon=D_{Cell}/D_{channel}$. One means for measuring the translation velocity of an agent is taught elsewhere in this specification.

The term "flow dynamics" refers to the wall shear rate, the flow rate, and the translational velocity of a specified particle within a moving fluid. To modify the flow dynamics, at least one of the aforementioned properties must be altered.

BRIEF DESCRIPTION OF THE DRAWINGS

The invention will be described by reference to the following drawings, in which like numerals refer to like elements, and in which:

FIG. 2A is a schematic view of capture device 10 with elongated ports and FIG. 2B depicts the removal of device 10 from the inlet and outlet ports;

Corresponding reference characters indicate corresponding parts throughout the several views. The examples set out herein illustrate several embodiments of the invention but should not be construed as limiting the scope of the invention in any manner.

DETAILED DESCRIPTION

A method is provided for sequestering a biological target from a donor in vivo, the method comprises utilizing an implanted target specific device, wherein the target specific device comprises a region comprising immobilized biological target specific binding agent. Internal fluid of the donor, which fluid is suspected of comprising biological target, contacts the device and biological target in the fluid interacts with the immobilized biological target specific recognition agent. The acts of recognition and interaction alter the flow characteristic of the bodily fluid in question. In one embodiment, the flow characteristic so varied is decreased; and this embodiment is preferred. In another embodiment, the flow characteristic is increased. One may so vary flow characteristics such as, e.g., the fluid velocity, the distribution of various components within the bodily fluid, and the shear stress of the fluid. The internal fluid of the donor may contact the lumen of the device directly and the biological target in the fluid may then bind to the target specific binding agent, or the biological target in the fluid may migrate across a semi-permeable membrane or layer from the bulk fluid to the capture zone and then bind to target specific binding agent. This migration may be encouraged through the use of a chemical attractant. The biological target may either be released from the lumen of the device for later use or neutralized whereby the body's own resources will later dispose of the neutralized cell.

Figure 1:
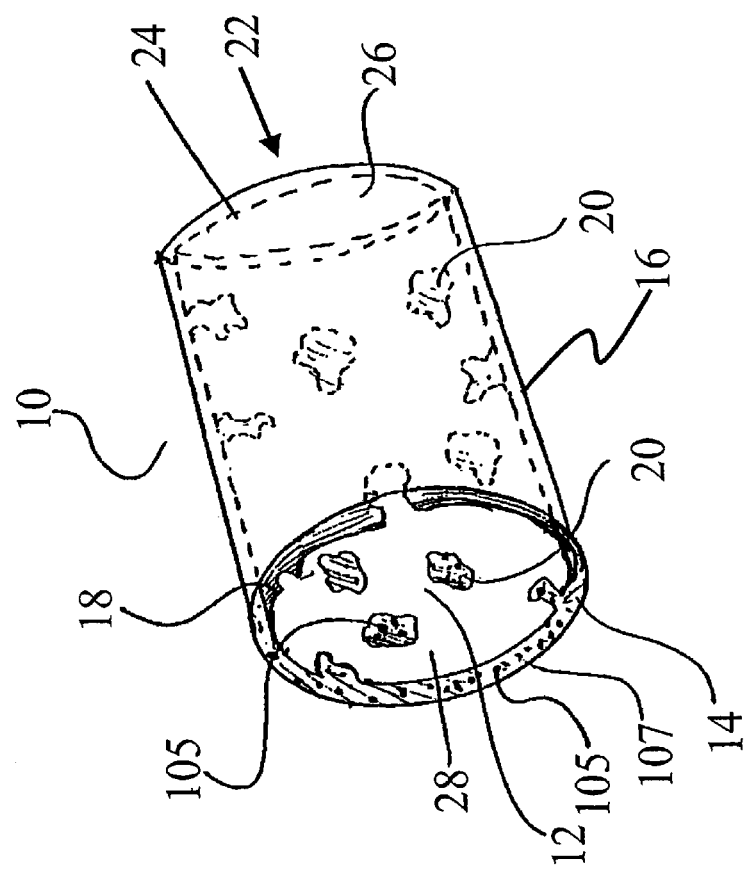
FIG. 1 is a schematic view of a cylindrical biological target specific capture device 10 that, in the preferred embodiment depicted, comprises a central fluid-conducting member 26, and a capture zone 14.
Figure 2:
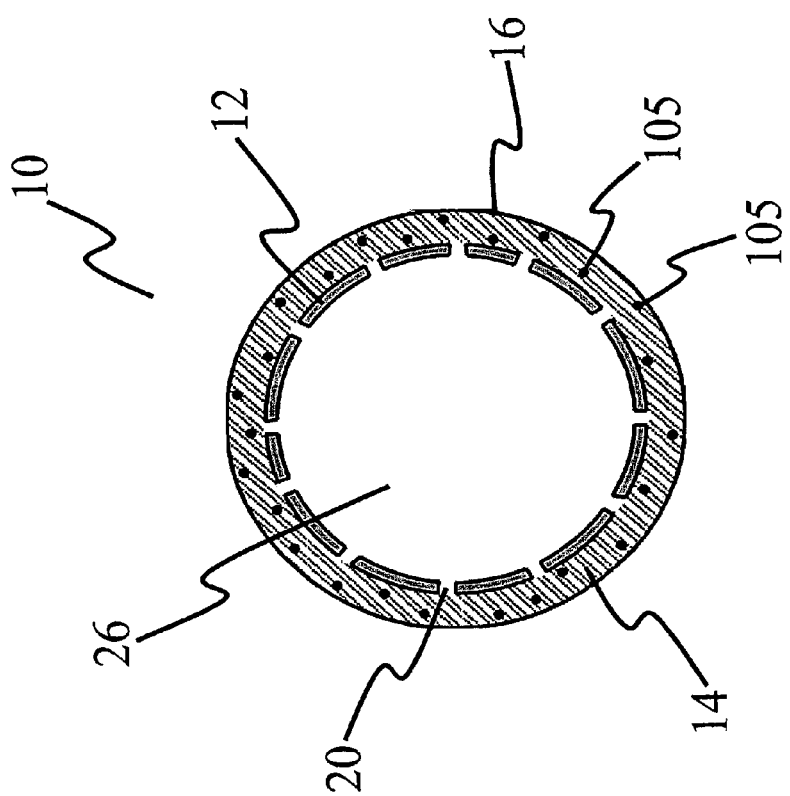
FIG. 2 is a sectional view of the capture device 10 depicted in FIG. 1.

FIG. 1 depicts a schematic view of one preferred device 10; as will be apparent, this Figure (and the other Figures in the case) are not necessarily drawn to scale. FIG. 2 depicts a cross sectional view of device 10. In the embodiment depicted in FIGS. 1 and 2, the device 10 is comprised of a zone 14 that is disposed between the outer wall 16 and permeable member 18. In the embodiment depicted, a binding agent 105 is disposed within inner wall 12 and chemical attractant 107 is disposed within zone 14. Permeable member 18 is adapted to allow one or more molecules to pass through it. Thus, it can be a permeable layer of material adapted to pass a specified biological target, or it can be a membrane. Permeable member 18 is preferably comprised of pores 20. Pores 20 may be any geometric shape, regular or irregular. At least some of pores 20 are large enough to permit biological targets to pass through and enter capture zone 14. In one embodiment, the pores 20 have a maximum cross-sectional dimension that is from about 30 microns to about 120 microns. The pores 20 have a pore size distribution such that the average pore size is of a value sufficient to enable biological targets, whose diameter on average is smaller, to pass through and enter capture zone 14. Referring again to FIG. 1, fluid (not shown) preferably flows in the direction of arrow 22 and enters inlet port 24. Thereafter, such fluid passes through central fluid-conducting member 26, and some of such fluid exits the outlet port 28. The inlet/outlet ports 24/28 are shown to be immediate with the boundaries on either side of the fluid-conducting member 26.

One of the characteristics of the bodily fluid that will be modified within the chamber 10 is its flow rate. The flow rate, also known as the volumetric flow rate (Q), may be determined by monitoring the displacement of a meniscus at the fluid/air interface in a calibrated microcapillary tube, as previously described in Fenton et al., Microvasc Res 29: 103-126, 1985. Alternatively the flow rate in the tube or in multiple tubes may be monitored using velocity phase-encoded Magnetic Resonance Imaging (see for example, Laukemper-Ostendorff et al., Journal of Membrane Science, 138: 287-295, 1988). Analysis of the device volumetric flow rate using Laser Doppler, radioisotope tracers or meniscus visualization is not possible for the measurement of the flow rate of a device with multiple tubes or with an opaque covering.

In general, the flow rate of the bodily fluid is decreased.

Referring again to FIG. 1, and in the preferred embodiment depicted therein, the chamber 10 preferably has an inner diameter 109 of from about 15 microns to about 150 microns. The chamber 10 need not necessarily have a cylindrical cross-sectional shape, in which case the maximum cross-sectional dimension 109 is from about 15 to about 150 microns.

The chamber 10 is preferably comprised of at least about 80 weight percent, or consists essentially of a biocompatible material. In one embodiment, the inner surface 12 is comprised of an antithrombogenic composition. Reference may be had, e.g., to U.S. Pat. No. 6,231,600, the entire disclosure of which is hereby incorporated by reference into this specification.

In one embodiment, chamber 10 is flexible.

In one embodiment of the invention, not shown, the inner wall of the chamber 10 is comprised of a matrix, and the matrix in turn is comprised of a binding agent. As used herein, the term binding agent is an agent that, in the presence of a particular biological agent, will interact with and sequester the biological agent so that such biological agent is no longer mobile. One can determine whether a binding agent immobilizes a particular biological agent by conventional protocols such as, e.g. immunocytochemistry.

By way of illustration, an antibody is a binding agent for an antigen. A peptide is a binding agent for a cell surface receptor. Reference may be had, e.g., to U.S. Pat. No. 6,399,063, and U.S. Pat. No. 6,177,542.

The device 10 (see FIG. 1) may be used to trap a particular biological agent.

As will be apparent, the device 10, with its capabilities, when used with bodily fluid comprised of a biological agent that it recognizes, causes a process to occur that is described hereinafter.

Figure 2A:
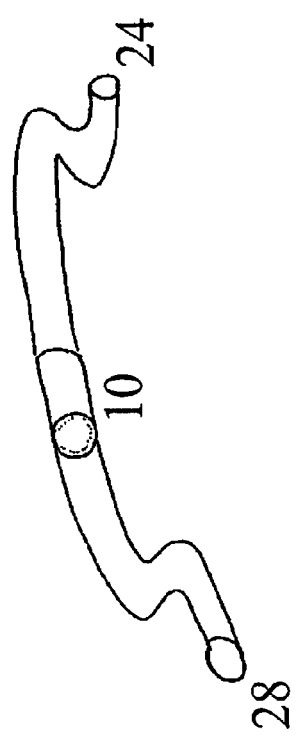

Referring to FIG. 2A, a schematic view of capture device 10, and as depicted in FIG. 2A, the inlet port 24 and/or the outlet port 28 of capture device 10 may be extended spatially, such that the port is separated in space from the fluid-conducting member; as long as the port is in fluid communication with the fluid-conducting member. In another embodiment, as shown in FIG. 2b the device 10 (FIG. 2) can be removed from the inlet port 24 and outlet port and replaced with an entirely separate device. The device 10 can be removed and flushed with the appropriate buffers to remove the biological agents for storage and later use or neutralization (not shown). Any of the binding agents disposed within the device 10 which may no longer be present or are not functional may also then be replenished with a the appropriate concentration of new and functional binding agents. The device 10 may then be reattached to the inlet port 24 and outlet port 28. In one embodiment the inlet port 24 will be a vascular graft attachment appropriately attached to an arterial feed line within a living being. The outlet port 28 will be a vascular graft attachment to venous supply within a living being. The appropriate attachment of shunts or vascular grafts is referenced elsewhere in this specification.

Figure 3:
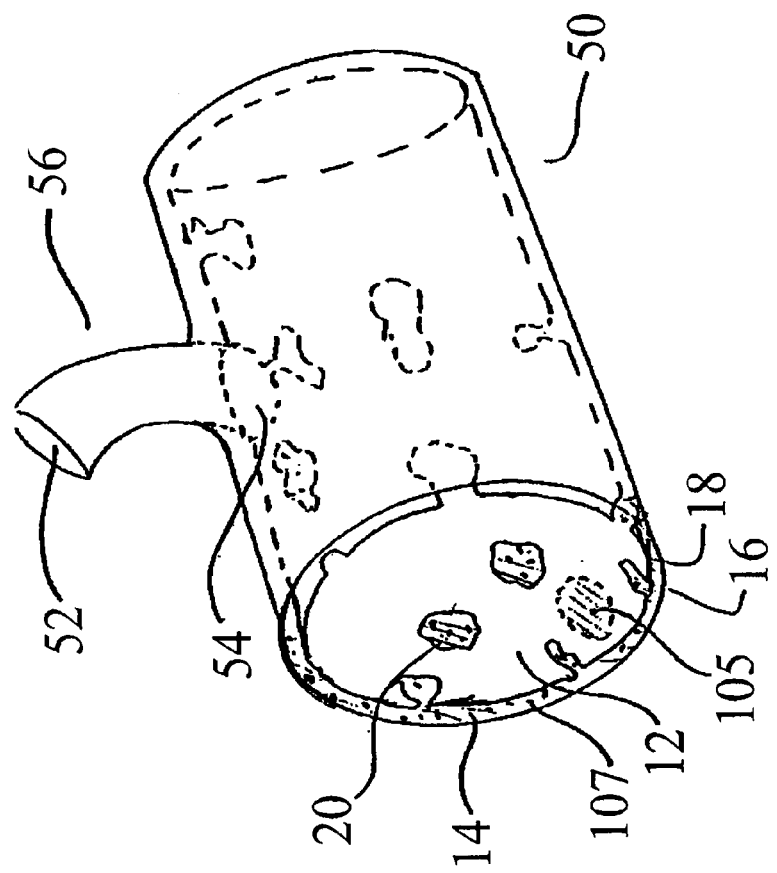
FIG. 3 is a schematic diagram of another preferred capture device 50 of the invention.

FIG. 3 is a schematic view of capture device 50. Referring to the embodiment depicted in FIG. 3, it can be seen that the capture device 50 is similar to capture device 10, but differs therefrom by the addition of access port 56. Access port 56 is in fluid communication with capture zone 14 by way of terminus 54; and it is also in fluid communication with terminus 52. The distance between terminus 52 and terminus 54 may be any length, as long as access port 56 is capable of being contacted with or is accessible to an externally supplied fluid-conducting device (not shown) such as, e.g., a syringe. In the embodiment depicted in FIG. 3, the binding agent 105 is disposed on the inner wall 109 of the device 50, and the chemical attractant 107 is disposed within the capture zone 14.

Figure 4:
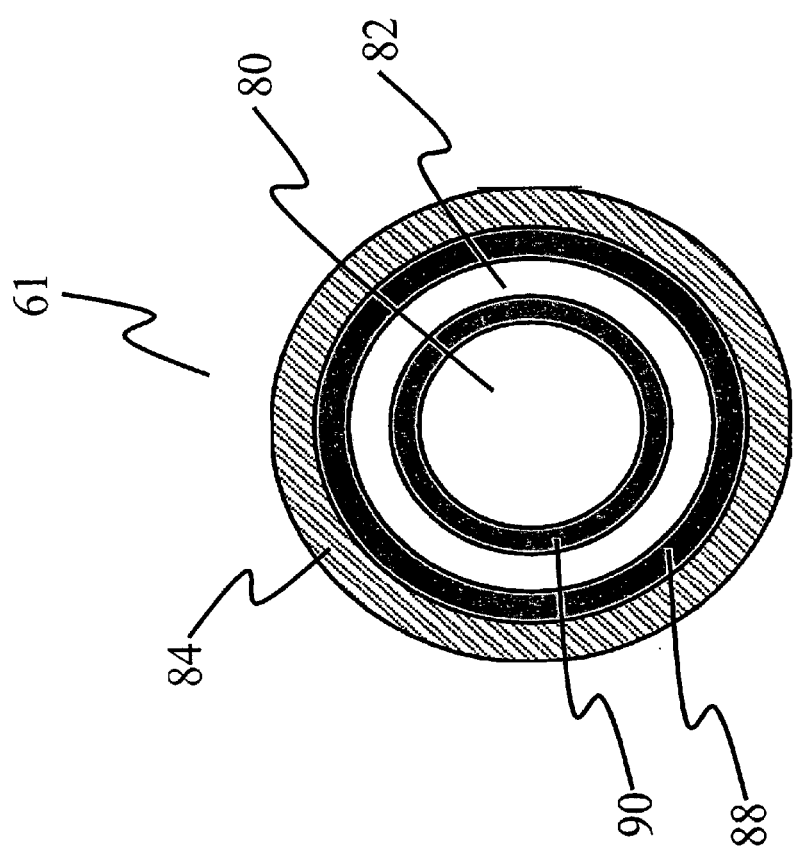
FIG. 4 is a sectional view of the capture device 61 that is similar to capture device 10 but differs therefrom in that, disposed outside of flow chamber 80 there are multiple permeable members, 88, and 90, and multiple capture zones (82 and 84)

FIG. 4 is a sectional view of the capture device 61 that is similar to capture device 10 but differs therefrom in that, central flow chamber 80 is encompassed by porous matrix 90, which in turn is encompassed by flow chamber 82. Likewise, flow chamber 82 is encompassed by porous matrix 88, which is encompassed by capture zone 84. The porosity of matrices 88 and 90 may be the same, or they may be different. In one embodiment, one or more of the binding agent(s) and/or the chemical attracting agents discussed elsewhere in this specification may be dispersed within one or both of such porous matrices 88 and 90 as well as in capture zone 84.

Figure 5:
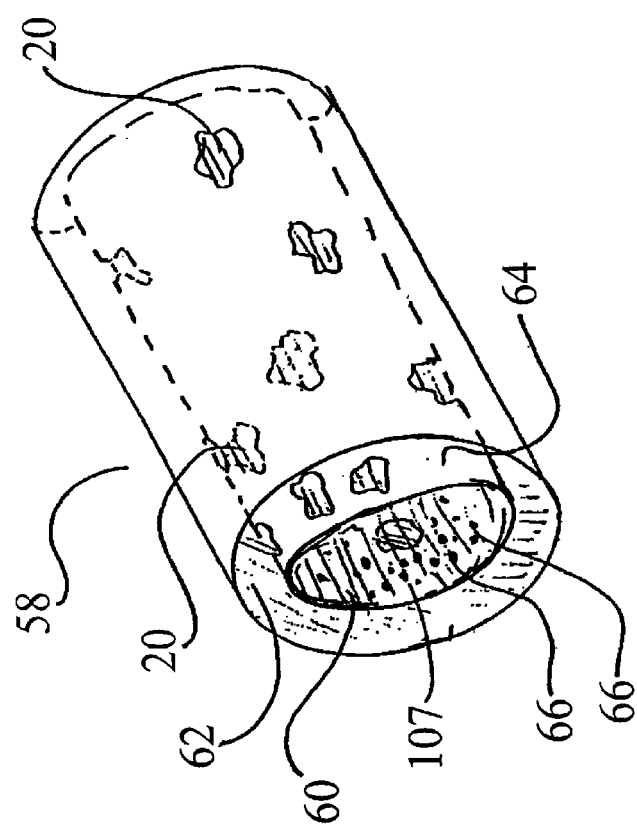
FIG. 5 is a schematic diagram of another capture device 58 of this invention.

Referring to FIG. 5, which is a schematic of another capture device 58 of this invention, and in the preferred embodiment depicted therein, the capture device 58 comprises a central, axial capture zone 60, a flow chamber 62, concentric with central capture zone 60 and separated therefrom by biological target permeable layer or membrane 64. In the embodiment depicted, a biological target specific binding agent 66 is immobilized in capture zone 60, as is chemical attractant 107.

Figure 6:
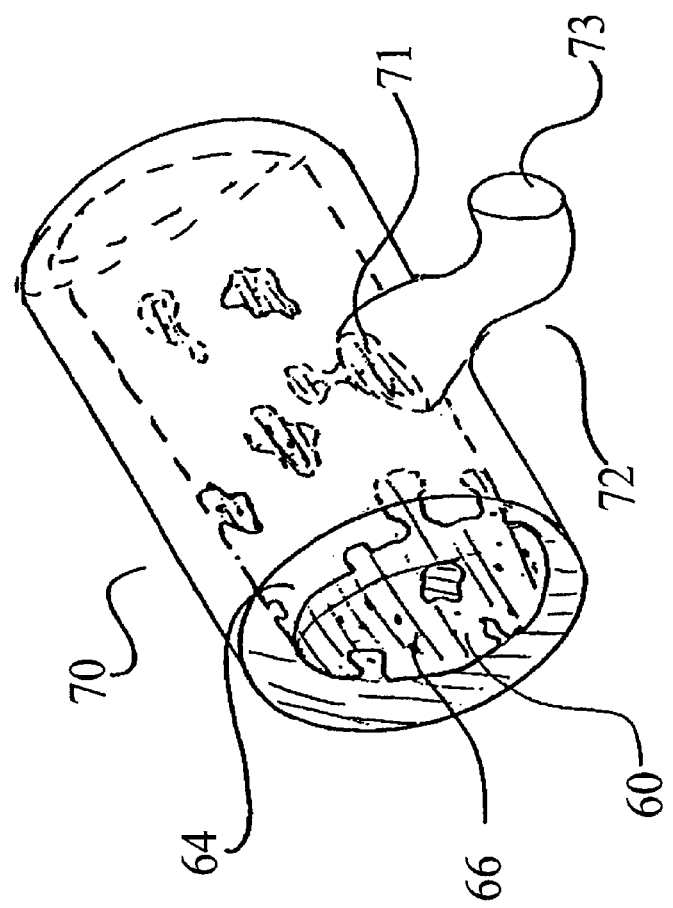
FIG. 6 is a schematic diagram of capture device 70. The biological target specific capture device further comprises access port 72 in fluid communication with central capture zone 60.

Referring to FIG. 6, which is a schematic view of capture device 70, and in the preferred embodiment depicted therein, it will be seen that capture device 70 is similar to capture device 58, but differs therefrom by the addition of access port 72 in fluid communication with central capture zone 60. Access port 72 is in fluid communication with capture zone 60 by way of terminus 71; and it is also in fluid communication with terminus 73.

Figure 7:
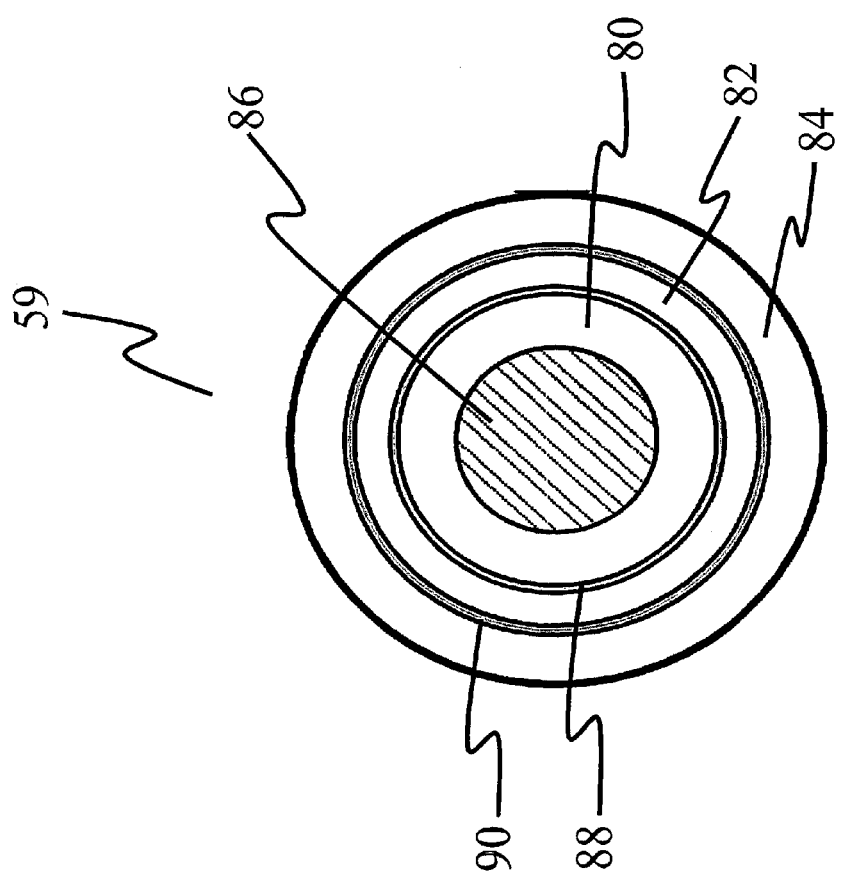
FIG. 7 is a sectional view of the capture device 59.

FIG. 7 is a cross sectional view of capture device 59. Referring to FIG. 7, it will be seen that capture device 59 is similar to capture device 58, but differs therefrom by the addition of a multiplicity of flow chambers 80, 82, and 84. Capture zone 86 is preferably disposed substantially coaxially with flow chambers 80, 82, and 84. Capture zone 86 is encompassed by flow chamber 80, which is encompassed by permeable member 88, which is encompassed by flow chamber 82, which is encompassed by permeable member 90, which is encompassed by flow chamber 84. The permeability of permeable members 88 and 90 may be the same, or they may be different. In one embodiment, one or more of the binding agent(s) and/or the chemical attracting agents discussed elsewhere in this specification may be dispersed within one or both of such porous matrices 88 and 90 as well as in capture zone 86.

Figure 8A:
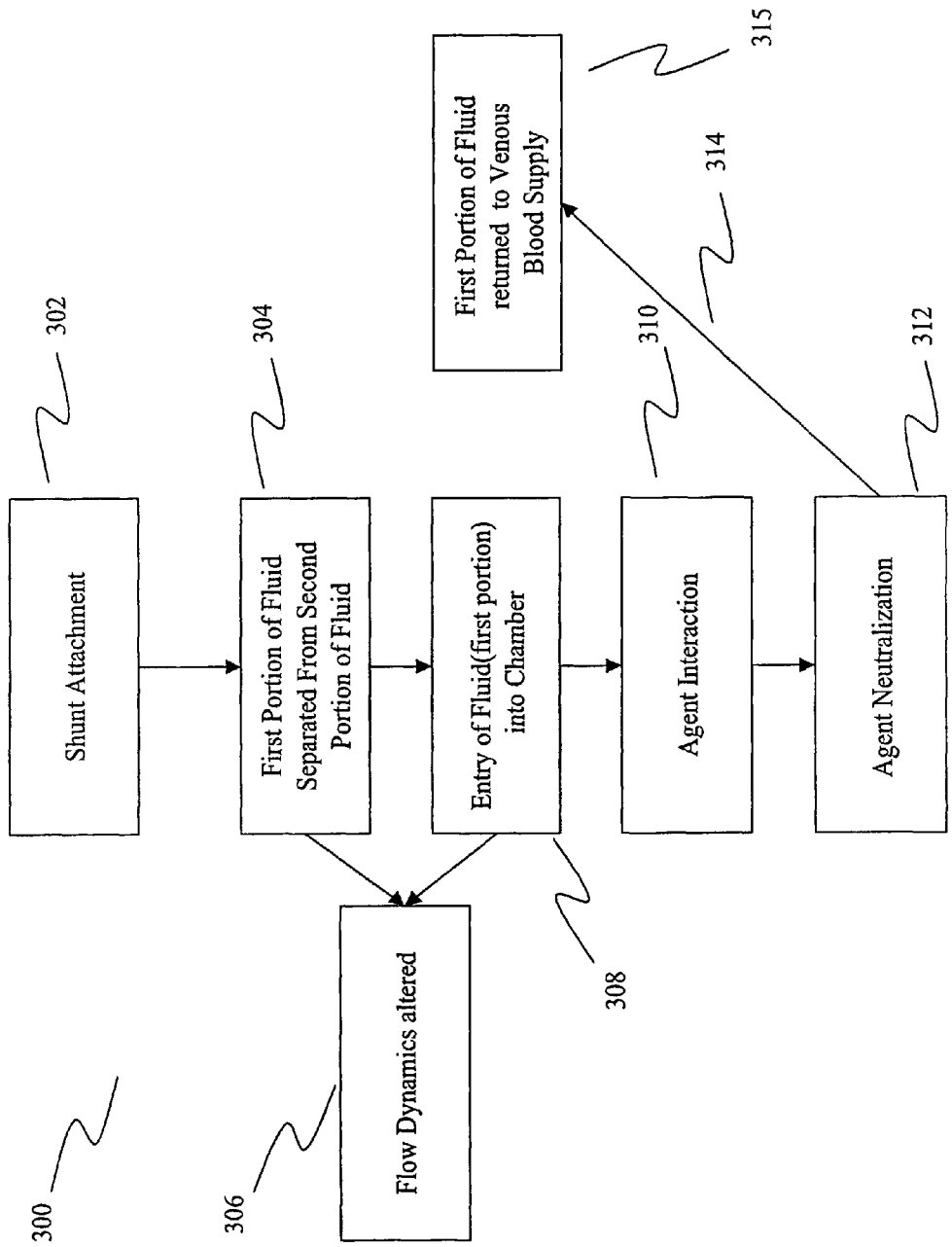
FIG. 8a is a flow diagram describing one of the preferred processes 300 in which diseased cells are identified and neutralized.
Figure 8B:
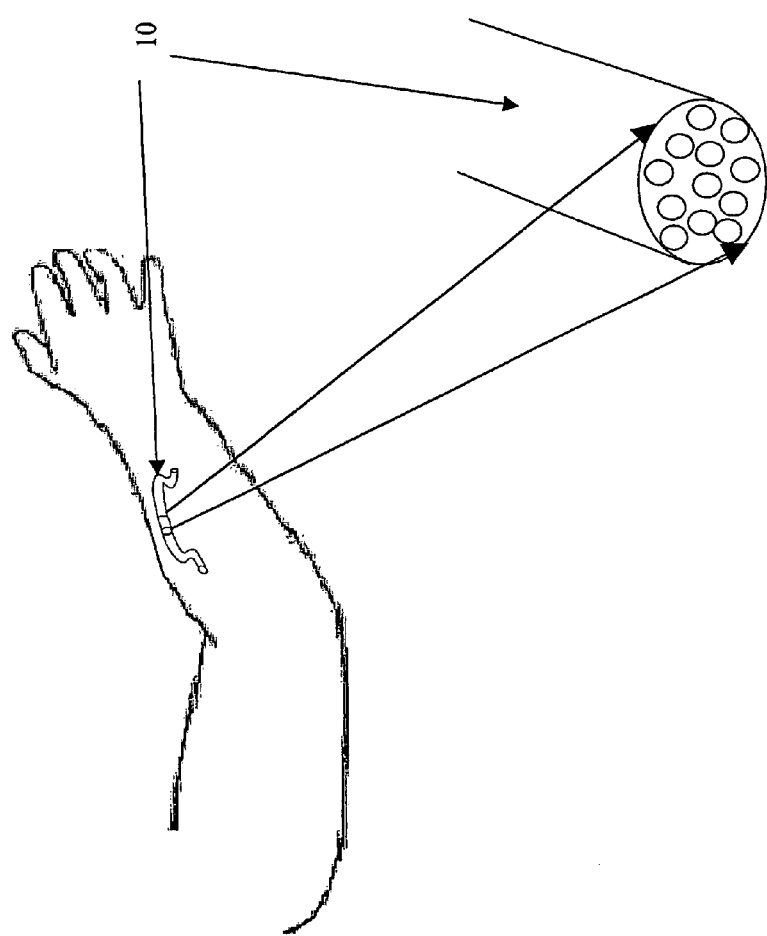
FIG. 8b is an illustration of one preferred method of attachment of the invention to a biological organism.

FIG. 8a is a flow diagram describing one process 300 of the invention in which diseased cells are identified and neutralized. Referring to FIG. 8a, and in step 302 thereof, an implantable device 10 is disposed within a biological organism. The deployment of the device 10 within a biological organism is illustrated in FIG. 8b. Thus, e.g., the device may an arterio-venous shunt, which communicates with an artery and vein and through which blood flows. The shunt may be surgically inserted by conventional means into a biological organism. One possible example of how a shunt may be deployed is shown in U.S. Pat. Nos. 5,755,775 ("Percutaneous stent-graft and method for delivery thereof"), or 4,559,039 ("Permanently placed transcutaneous access device to blood vessels").

Blood is but one example of a biological fluid that may be treated by the process of this invention. Other biological fluids include, e.g., bone marrow, lymph, urine, bile, cerebral spinal fluid, and the like. For purposes of simplicity of description of this embodiment, blood will be referred to as the biological fluid.

In one step of the process of this invention, the blood is divided into a first portion and a second portion. Thus, and referring again to the embodiment depicted in FIG. 8b, the shunt in vivo will cause a percentage of the bodily fluid to flow through the device 10, with another percentage of the fluid flowing into the venous blood supply. Thus, in step 304, a first portion of fluid is separated from a second portion thereof.

This separation of the bodily fluid into at least two portions will cause the flow dynamics of the bodily fluid to change (see step 306), especially as the first portion of the fluid enters into the chamber in step 308. When the flow dynamics is altered it is meant that the shear rate, flow rate, and the biological agent translational velocity of bodily fluid are modified in the first chamber. As used herein, the term modified means increase or decrease.

Applicants have developed a protocol for making in vitro measurements and determinations relating to the system disclosed in the drawings and the specification. This protocol is briefly described below.

In this protocol, the inner diameter of the flow channel is preferably measured from images captured with video microscopy with a spatial calibration using a stage micrometer.

In this protocol, the wall shear rate is calculated using the flow rate and channel diameter based on Poiseuille's Law where shear rate=$32Q/D^3$.

In the current description, the biological agent is defined as a metastatic cancer cell. The cancer cell velocity is measured using stop frame video microscopy. Digitized images of translating cells are captured sequentially at known time intervals. Velocity is determined from the particle displacement over the sampled time interval. A spatial calibration for the optics used in each experiment is acquired with a stage micrometer and applied to displacement measurements to yield absolute units.

In this protocol a circulating cell is deemed to be marginated (or have a rolling flux) based on its translational velocity. Rolling flux is quantified as all observed cells translating a velocity below the hydrodynamic velocity for the given size channel and driving pressure at a position 1 cell radius from the channel wall (the critical velocity). This value is calculated from the 1-D solution of the Navier-Stokes equation for flow in a cylinder: $V_{crit}=(2Q/D^2)\epsilon(2-\epsilon)$ where $\epsilon=D_{cell}/D_{channel}$.

In this protocol the total flux of circulating cancer cells is calculated from the concentration of cancer cells, determined by a count using a hemocytometer, and the volumetric flow rate for each experiment. The following are considered as non-limiting examples of the protocols that may be used in determining one preferred practice of this invention:

For in vitro verification, fluorescently labeled cancer cells, prepared as known to those skilled in the art, are mixed with anticoagulated whole blood (104 cells/ml will provide sufficient numbers for observations) and flowed through channels across the range of diameters. Microcapillary tubes are made ranging in diameter from 20 to 100 mm in approximately 10 mm increments. For each diameter flow channel, margination measurements are made at three axial positions to determine if an optimal length and diameter exists for facilitation of interaction of the circulating cancer cell and the attraction agent (see FIG. 9, locations 330, 332 and 334). At least three flow trials are conducted for each diameter channel with a trial lasting a period 10 minutes. Pressure driving forces are limited between 80 and 40 mmHg to simulate the pressure drop across an arterial-venous shunt in a human. The driving pressure of interest is that which can be established across an arterial-venous shunt, where the tested technology is intended to work. Therefore, the tested driving pressures may be higher than values observed in the circulation of organ systems where metastases occur or in native tumors (10-40 mmHg).

Blood is used at a physiological hematocrit of 0.45; however, whole blood can be diluted to reduce hematocrit to levels consistent with human patients undergoing chemotherapy or radiation therapy. Flow channels are observed under fluorescence excitation light to observe calcein loaded cells (480/510 nm) on an inverted microscope equipped for fluorescence optics to visualize the number of marginated cells.

The number of marginated cancer cells normalized for total cancer cell flow are calculated and evaluated as a function of flow rate and tube diameter to show the optimal geometry for facilitation of cancer cell interaction with the flow channel wall. These empirical data show the optimal geometry determined by the number of marginated cancer cells per time.

As a control, the effluent is centrifuged to isolate the plasma to be analyzed for indications of shear induced red blood cell hemolysis by spectroscopy. If detectable, levels of hemolysis are correlated to respective wall shear rates for each flow experiment.

Marginated cancer cells are identified as those with a translational velocity below the critical hydrodynamic velocity at a radial position one cell radius from the wall. This critical velocity is determined from the solution of Navier-Stokes equation for 1-dimensional flow under respective pressure driving forces specific to each trial, as previously demonstrated.

Figure 9:
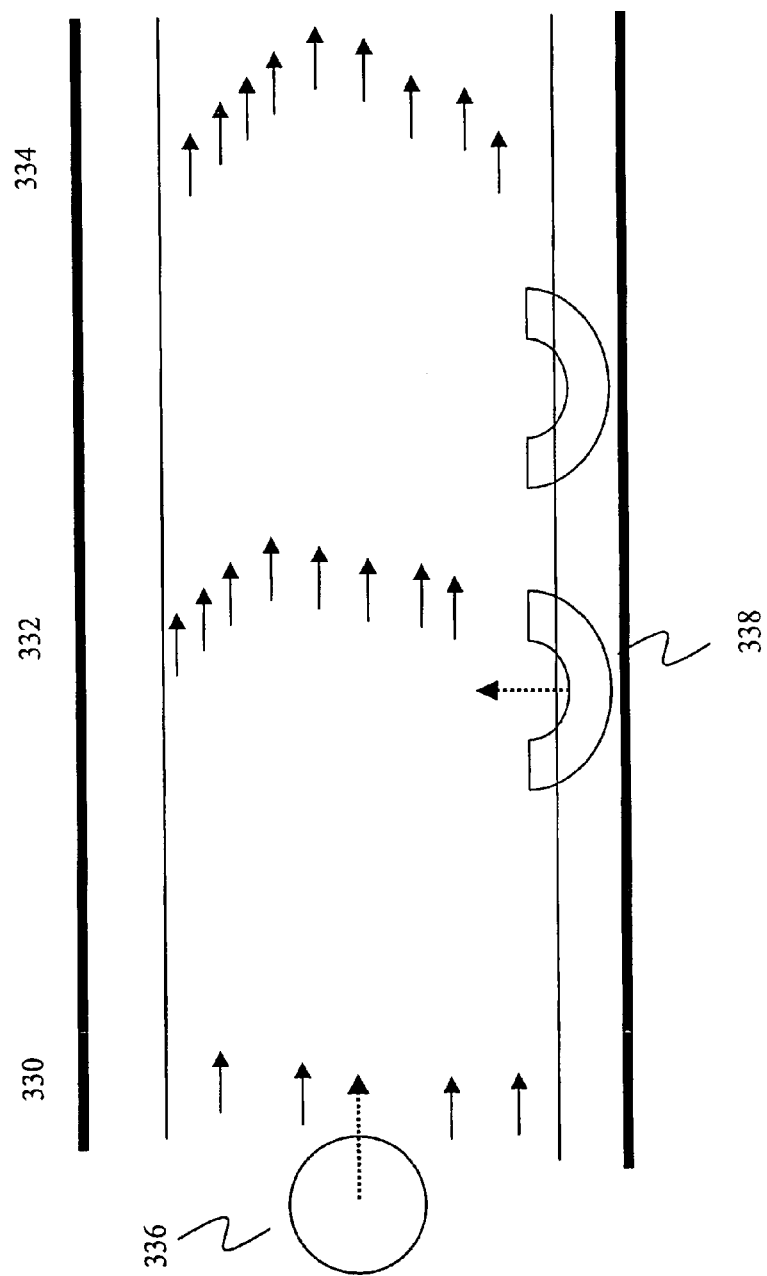
FIG. 9 is a simplified illustration of a preferred method for biological agent entry into a capture device.

The total delivery of cancer cells is calculated from the flow rate and the known concentration of cancer cells in the feed. Translational velocity is measured from digitized images. Referring to FIG. 9, the process of metastatic cancer cell (336) entry into the chamber.

The effectiveness of each flow channel in facilitating margination, which ultimately indicates the effectiveness in exposing cancer cells to a neutralizing agent, is determined by the screening rate and screening efficiency. The screening rate will be calculated as the number of marginated cells/unit time and represents the total number of cells that are treated. The screening efficiency is calculated as the number of marginated cancer cells/delivered cancer cells.

Figure 10:
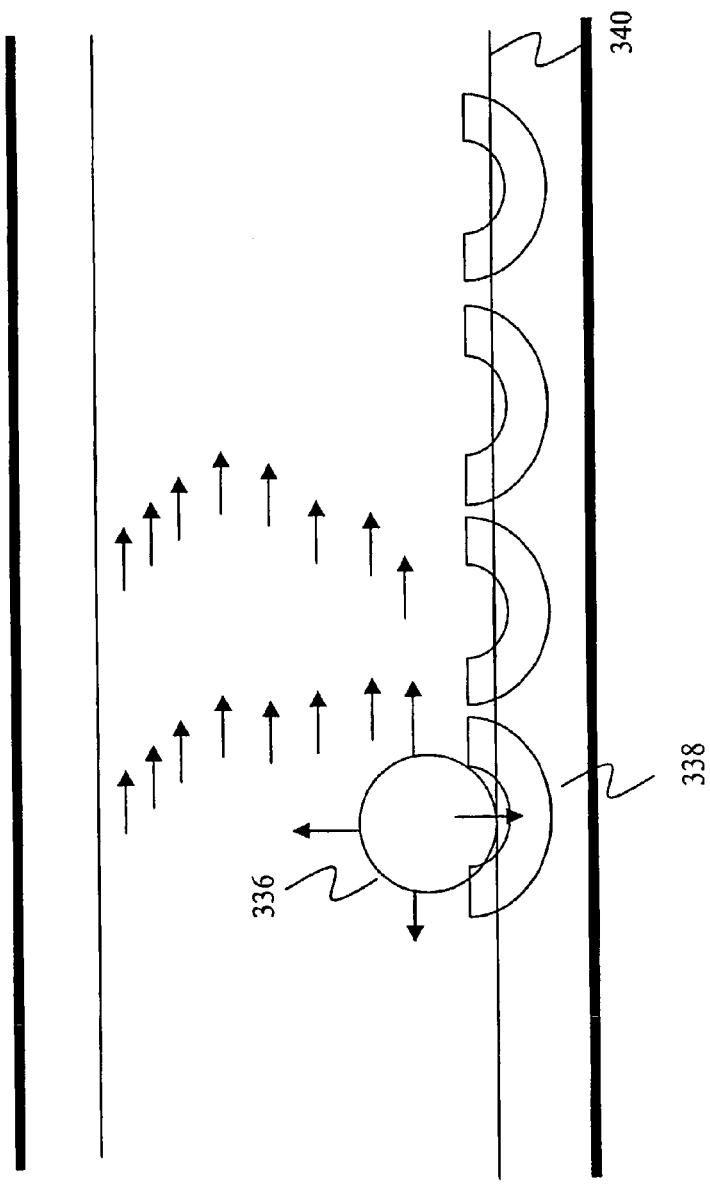
FIG. 10 is a simplified illustration of a preferred method for biological agent interaction with a biological attachment agent and margination within the capture device.
Figure 11:
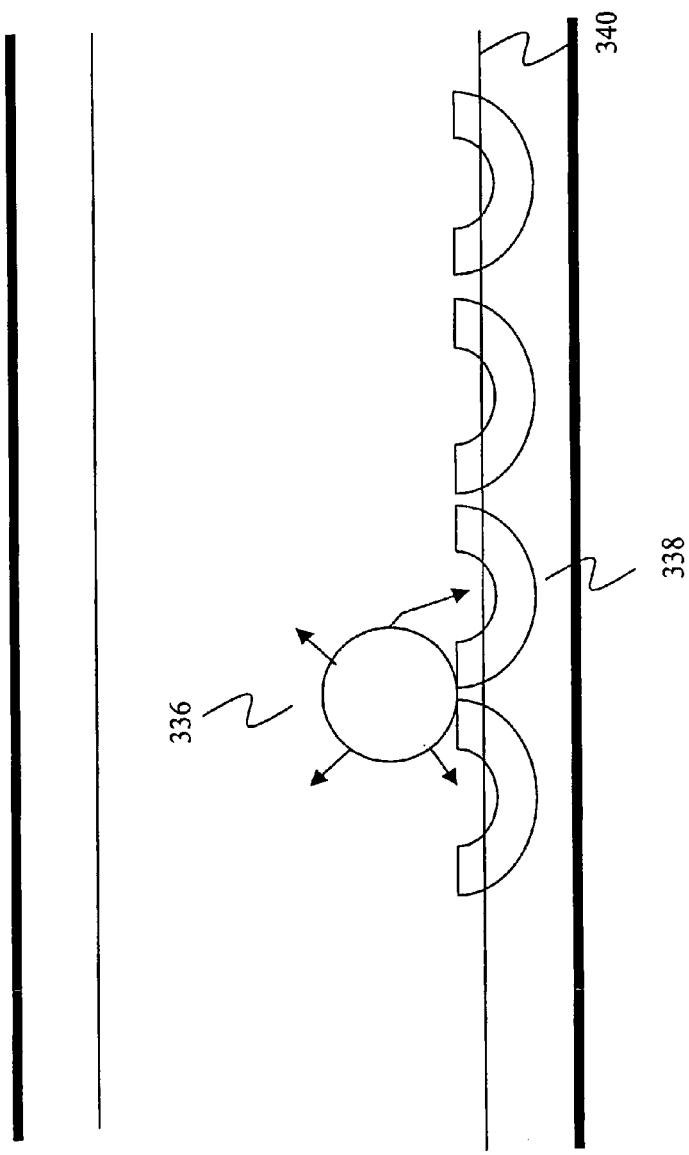
FIG. 11 is a simplified illustration of one preferred method of biological agent rolling along the biological attachment agents in the capture device.

Enhancement of the geometric mechanism for the isolation of target cancer cells from the circulating cellular components of whole blood is done by addition of target specific binding agents to facilitate molecular interactions between the cancer cells and the attraction agents adhered to the flow chamber wall. FIG. 10 is a simple depiction of one method by which a metastatic cancer cell (336) can interact with a target specific binding agent (338). FIG. 11 then illustrates one method of flux rolling of a metastatic cancer cell along the target specific binding agent (338) adhered to the chamber wall (340). One preferred embodiment uses the adhesion molecule E-Selectin as a target specific binding agent with adhesive properties that are favorable towards binding tumor cells. Other molecules, including P-selectin, ICAM-1, and cadherin-11, can also be used as target specific binding agents to enhance interactions between circulating cancer cells and the flow channel surface. Flow channels of the optimal geometry, as determined earlier in this protocol, are augmented with a target specific binding agent recognized to facilitate transient interactions between tumor cells and blood vessels in vivo, in order to increase the exposure time to the flow channel wall. A target specific binding agent is immobilized on the luminal surface of the flow chamber using a simple adsorption process as known by those skilled in the art. Subsequently, the flow channel is incubated with a 2% solution of bovine serum albumin to block nonspecific binding. This method of adhesion molecule immobilization has been previously demonstrated with the cell adhesion molecule E-selectin to initiate rolling of the cells expressing the carbohydrate moiety siayl-Lewis (Slex) including neutrophils and immortalized cancer lines under flow conditions, in a site density-dependent manner (Glycobiology, vol. 4, pp. 259-265, 1994).

The site density is tuned by adjusting the protein concentration of the adsorbed solution to regulate the exposure time of interacting cells to the adsorbed surface. The contribution of non-specific binding events is determined by blocking adsorbed target specific binding agent with antibodies. In addition to observations of interaction between cells and the flow channel surface, the effectiveness of target specific binding agent adsorption is determined using immunofluorescence labeling and optical assessment of the uniformity of fluorescence emission.

To determine the optimal effective site density of adsorbed target specific binding agent, MDA-MB-435 human breast carcinoma cells, suspended in serum free culture media (105/ml-high concentration to facilitate observation of interacting cells) are perfused at flow rates resulting in wall shear stresses exceeding the limits observed to facilitate leukocyte rolling equivalent to $\tau_w > 2$ dyn/cm², which correspond to flow conditions tested earlier in this protocol for optimal channel diameter. This reduces the potential for damage of desirable blood components, namely leukocytes, which can also exhibit binding to adsorbed target specific binding agents such as E-selectin. Additionally, the high shear forces imparted on the interacting tumor cells can cause mechanical damage, thereby contributing to the neutralization of tumor forming potential. Cell interactions are observed with bright field microscopy and recorded for offline analysis of interaction behavior. The translational velocity of cancer cells captured by the treated surface is measured and the concentration of adsorbed target specific binding agent adjusted to maximize transit time and to increase exposure to the therapeutic agent without occluding flow. To determine this optimal site density, the site density of adsorbed target specific binding agent will be increased incrementally based on the previous measurements until average translational velocities fall below 3 mm/s (which results in a 15 minute exposure over 2 cm of channel length) or until firm arrest occurs. In the presence of firm arrest, a decreased site density is used until the translational velocity criterion is met.

Tumor cell targeting using the geometric constraints and adhesion molecule immobilization described earlier in this protocol prolongs the exposure of the isolated cell to the flow chamber surface. By adsorbing a high surface density of an anti-proliferative agent to the flow channel surface, the tumor forming capacity of the isolated cells is neutralized during the transit time for passage, while limiting systemic exposure to potentially harmful doses of the anti-proliferative agent.

In one preferred embodiment, the anti-proliferative agent is paclitaxel, which is known to inhibit migration and proliferation of tumor cells. Paclitaxel suppresses mitogenic activity in cells by stabilizing microtubule polymerization leading to arrest in the G2/M phase of the cell cycle. The flow channel of optimal size, as determined earlier in this protocol, is coated with high concentrations of paclitaxel by evaporation from a volatile solvent (>150 mg/ml paclitaxel in ethanol), rinsed with sterile filtered water, and dried overnight. Uniformity of coating between channels is verified at random by extracting the coated paclitaxel and assessing concentrations using HPLC as described by Heldman et al. The paclitaxel-coated flow channel is then coated with E-selectin to the optimal site density, as determined previously in this protocol. It has been previously shown that implanted stents coated with this method and placed in porcine coronary arteries resulted effective prevention of neointimal proliferation after 4 weeks, demonstrating an effective means of localized drug delivery to prevent proliferation of interacting cells (Circulation, volume 103 (18), pps. 2289-95, 2001).

Flow experiments are conducted using whole blood spiked with fluorescently labeled cancer cells. To provide sufficient material for analysis, a high concentration of cancer cells (106 per ml) are used. In some cases, cancer cells are labeled with a nuclear dye (DAPI, Molecular Probes) to retain fluorescence after fixation and membrane extraction for microtubule staining. The cancer cell-inoculated blood is perfused through the flow channel using the pressurized flow system. A range of perfusion pressures from 40 to 80 mmHg are studied in randomized runs to simulate the characteristic range of driving pressures between a peripheral artery and vein (assuming 120 to 80 mm Hg for artery and approximately 40 mm Hg in veins). Perfusion is maintained at constant driving pressure for 10 minute intervals. During perfusion, the flow through the channel is observed using fluorescence video microscopy and recorded to SVHS for offline analysis. From the recorded images, the number of interacting cells and the total number of perfused cells are counted to determine the population of treated cells. In addition, the total number of perfused cells is also determined from the effluent.

The effectiveness of the paclitaxel exposure in neutralizing the metastatic capacity of the eluted cancer cells is evaluated by several means. All analyses are conducted in parallel with cells treated in a sham procedure where cells are perfused through a flow channel without paclitaxel. The number of viable cells is estimated from samples of number of viable cells counted in the diluted effluent multiplied by the dilution factor. This number is divided by the total flux to assess the efficiency of cancer cell neutralization.

As described elsewhere in this specification, the biological agents within the bodily fluid that enter the chamber (in step 308) will be recognized by the binding agent(s) disposed on the surface or within the chamber and will interact with one or more of these binding agents in step 310. FIG. 8 is a depiction of the steps leading to the interaction of the biological agents with the binding agents.

In the embodiment illustrated in FIG. 8, some or all of the biological agents that interact with the binding agent(s) are neutralized in step 312. In one aspect of this embodiment, some or all of the cells thus neutralized are returned to the venous blood supply 315, in process 314, and then, optionally, recycled back through the biological organism. A portion of this recycled fluid eventually will again pass through the shunt attachment wherein the process can be repeated indefinitely. As will be apparent, this process allows multiple interactions between the biological agents and the binding agents and thus increases the efficiency of metastatic tumor cell identification and neutralization.

In one embodiment, the bodily fluid containing the biological agent will pass through the shunt at least twice. In another embodiment, the bodily fluid containing the biological agent will pass through the shunt at least four times.

Figure 12:
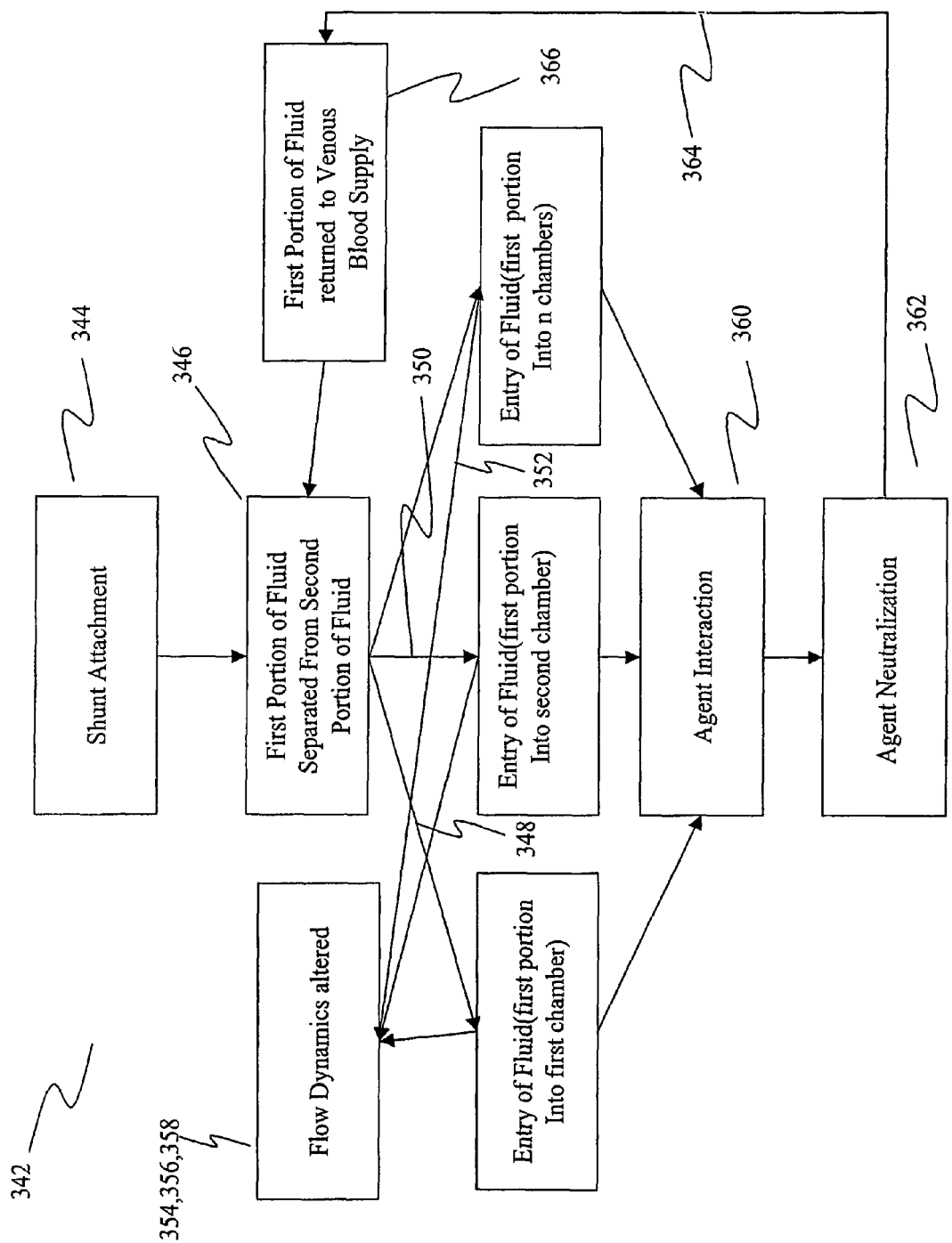
FIG. 12 describes another preferred process 342 which is a modified version process 300.

In one embodiment the process 342 shown in FIG. 12, is a modified version of the process 300 depicted in FIG. 8a. As in the process 300, the device 10 is disposed within a living being in step 344 in the same manner as step 302 in FIG. 8a. Still referring to FIG. 12 blood is divided into a first portion and into a second portion in step 346 such that a percentage of the first portion of blood is preferably fed into a first chamber, and a percentage portion of blood defined as the second portion remains within the systemic circulation. In one aspect of this embodiment, the first portion of blood is fed into a first chamber (348) and the second chamber (350) which is disposed within a third chamber, and each of the first chamber and the second chamber has a maximum cross-sectional dimension of 100 microns and an inner wall. In one aspect the first portion of blood may enter multiple chambers, n, disposed within the third chamber (352) wherein n defines a number for a multiplicity of chambers. In one embodiment, the integration of these chambers will result in the composition of device 10. As in step 306 in FIG. 8a and again referring to FIG. 12 the fluid dynamics of the first portion are altered in steps 354, 356 and 358. As in step 310 of the process described in FIG. 8a, the step 360 in FIG. 12 will comprise of the bodily fluid entering one, two or a multiplicity of chambers, n, (steps 348, 350, 352) followed by the biological agents within the bodily fluid interacting with one or more binding agents disposed on the luminal surface of one, two or n chambers (step 360) through the processes of margination, flux rolling and/or binding (defined previously in this specification). In this embodiment the preferred biological agents are either a metastatic cancer cell or any other diseased cell type, which may be harmful to the living being. Referring again to FIG. 12, in step 364 the biological agents (cells) will then be neutralized by being exposed to a toxic agent (ie. paclitaxel) also disposed on the luminal surface of one, two or a multiplicity, n, chambers within the third chamber. Referring again to FIG. 12, as in the process of steps 314 and 315 in FIG. 8*a* the neutralized biological agents along with the bodily fluid and all other components within that fluid can be returned to the venous blood supply as in steps 364 and 366. In one embodiment the device 10 described within the processes on page 13, will be removed from the arterial and venous attachments and flushed with the appropriate buffers for the removal of cells, cellular particles, cellular debris, fibrin and other large macromolecules typically found in circulating bodily fluids, which are bound to the luminal surface of one, two or the multiplicity, n chambers. In this embodiment the binding agents and any other required matrix materials which were removed during device function or flushing will be replaced at the appropriate spatial concentration. In another embodiment the device 10 can be replaced with a completely separate device where the original is disposed of.

Figure 13:
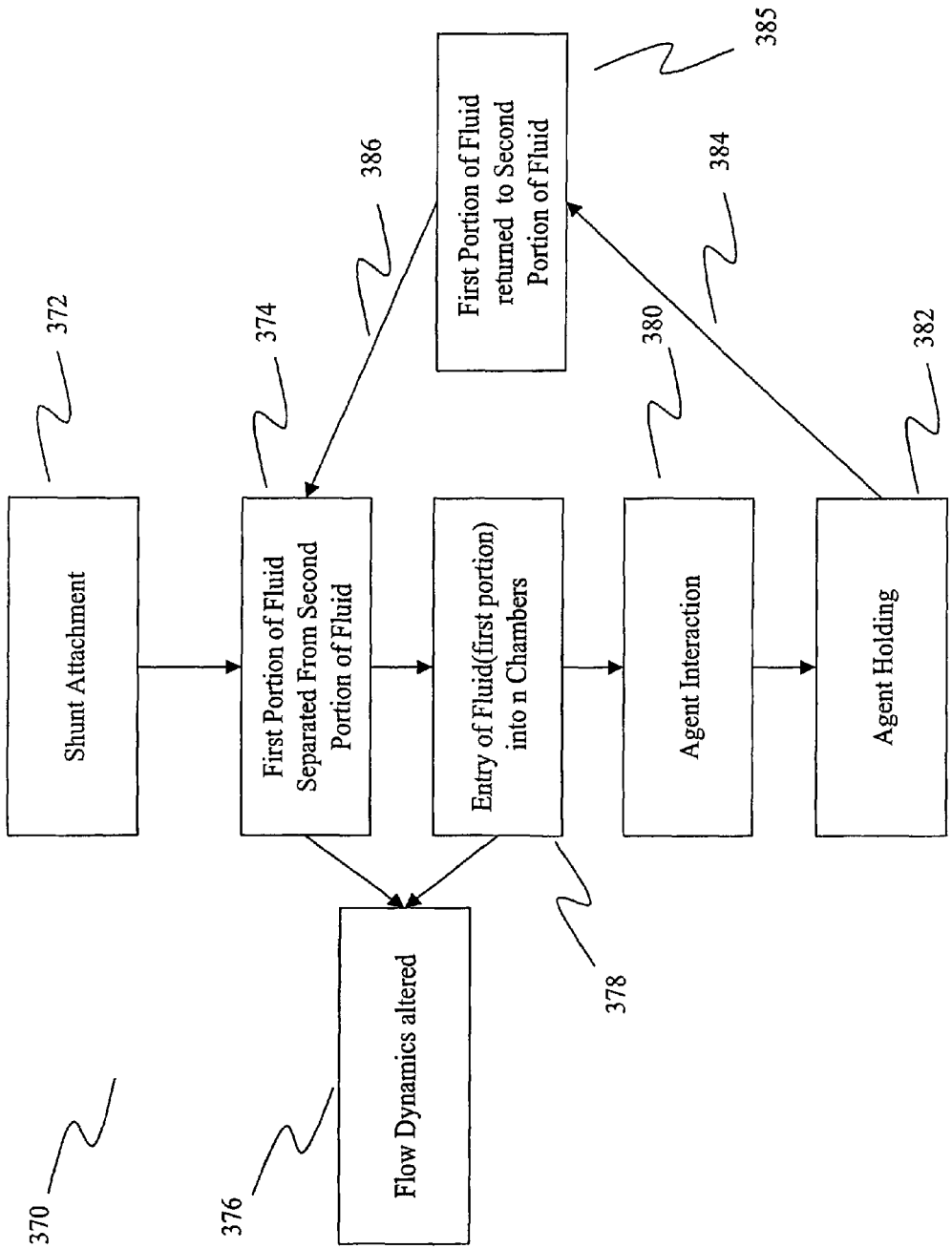
FIG. 13 describes another preferred process 370 in which any circulating cell can be identified, bound temporarily and then extravasate to a capture zone.

In one embodiment the process 370 shown in FIG. 13, is a modified version of the process 300 depicted in FIG. 8*a*. As in the process 300, the device 10 is disposed within a living being in step 372 in the same manner as step 302 in FIG. 8*a*. Still referring to FIG. 13 blood is divided into a first portion and into a second portion in step 374 such that a percentage of the first portion of blood is preferably fed into a multiplicity of chambers, n, or in other words into the device 10 described in FIG. 12. A percentage portion of blood defined as the second portion will then remain within the systemic circulation. As in step 306 in FIG. 8*a* and again referring to FIG. 13 the fluid dynamics of the first portion are altered in step 376. As in step 310 of the process described in FIG. 8*a*, the step 378 in FIG. 13 will comprise of the bodily fluid entering a multiplicity of chambers, n, followed by the biological agents within the bodily fluid interacting with one or more binding agents disposed on the luminal surface of n chambers (step 380) through the processes of margination, flux rolling and/or binding (defined previously in this specification). In this embodiment the preferred biological agents are cells which may be pluripotent stem cells or immune cells of various types. Binding of these cells will eventually be fixed following any flux rolling or margination of the biological agents which may occur along the luminal surface of the multiplicity of chambers, n in the process 382 termed "Agent Holding" in FIG. 13. Referring again to FIG. 13, as in the process of steps 314 and 315 in FIG. 8*a* a portion of biological agents, which are unbound along with the bodily fluid and all other components within that fluid, can be returned to the venous blood supply in steps 384 and 385. In one embodiment of this invention (not shown) the pluripotent stem cells will be bound in a temporary fashion and used in the local vicinity of the device for tissue regeneration. The in vivo isolation of stem cells using different methods and later used for tissue regeneration is described in the international application WO03040336 ("STEM AND PROGENITOR CELL CAPTURE FOR TISSUE REGENERATION"). In one embodiment the device 10 described within the processes on page 14, will be removed from the arterial and venous attachments and flushed with the appropriate buffers for the removal of cells, cellular particles, cellular debris, fibrin and other large macromolecules typically found in circulating bodily fluids, which are bound to the luminal surface of one, two or the multiplicity, n chambers. In this embodiment the binding agents and any other required matrix materials which were removed during device function or flushing will be replaced at the appropriate spatial concentration. In another embodiment the device 10 can be replaced with a completely separate device where the original is disposed of.

Figure 14:
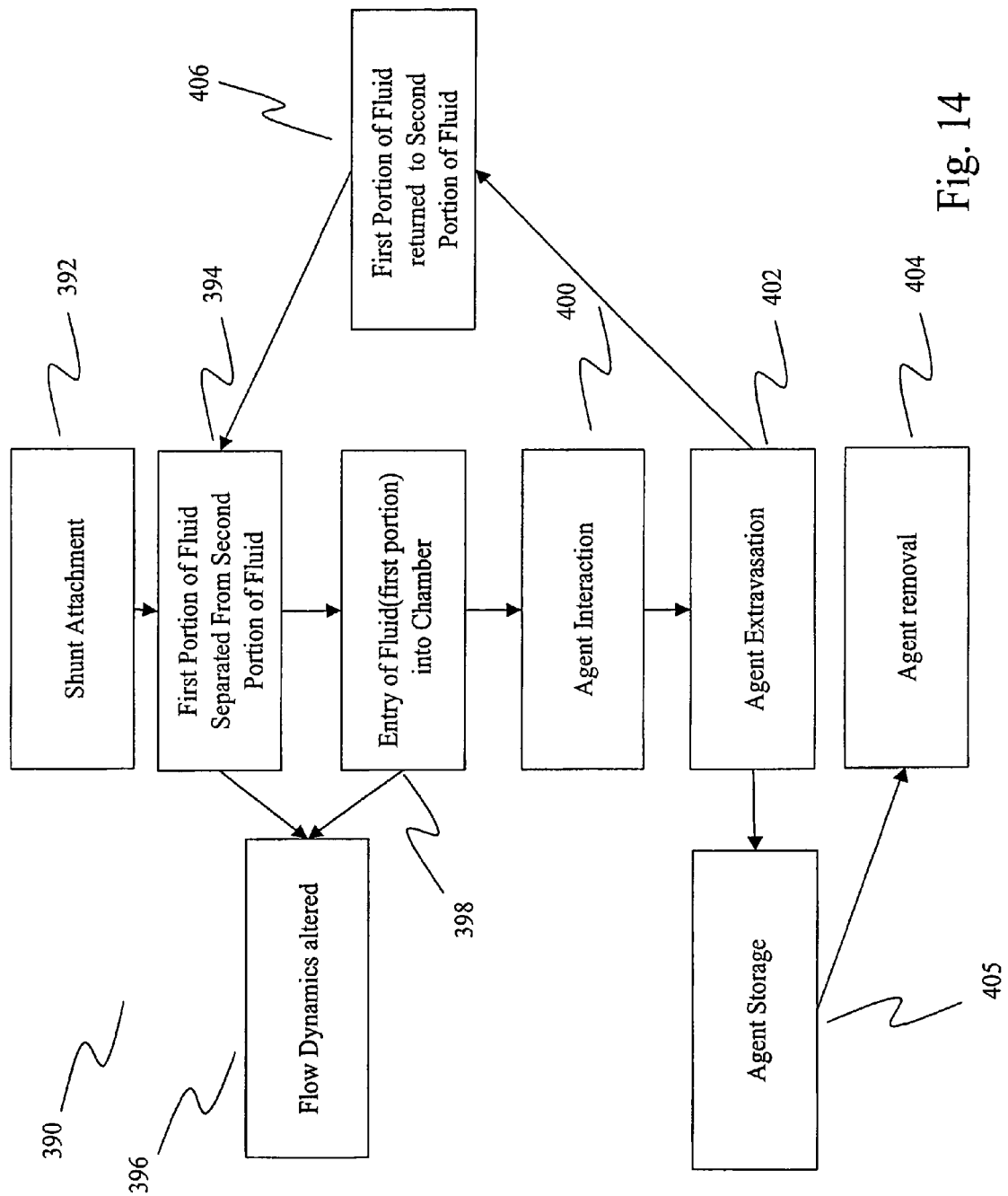
FIG. 14 is another modified form of process 300.

In one embodiment the process 390 shown in FIG. 14, is another modified version of the process 300 depicted in FIG. 8*a*. As in the process 300, the device 10 is disposed within a living being in step 392 in the same manner as step 302 in FIG. 8*a*. Still referring to FIG. 14 blood is divided into a first portion and into a second portion in step 394 such that a percentage of the first portion of blood is preferably fed into a multiplicity of chambers, n, or in other words into the device 10 described in FIG. 14. A percentage portion of blood defined as the second portion will then remain within the systemic circulation. As in step 306 in FIG. 8*a* and again referring to FIG. 14 the fluid dynamics of the first portion are altered in step 396. As in step 310 of the process described in FIG. 8*a*, the step 398 in FIG. 14 will comprise of the bodily fluid entering a multiplicity of chambers, n, followed by the biological agents within the bodily fluid interacting with one or more binding agents disposed on the luminal surface of n chambers (step 400) through the processes of margination, flux rolling and/or binding (defined previously in this specification). In this embodiment the preferred biological agents are cells which may be pluripotent stem cells or immune cells of various types. In this embodiment, a permeable or porous member(s) also disposed on the luminal surface of the multiplicity of chambers, n, may or may not be used to allow selective exposure of the binding agent. As described, the biological agents within the bodily fluid will interact with one or more binding agents disposed on the luminal surface of n chambers (step 400) through the processes of margination, flux rolling and/or binding (defined previously in this specification) and may or may not be incorporated into the pores of the permeable or porous material. A chemical attractant(s) may or may not be used to encourage migration of the biological agent across the permeable member(s). This migration is shown in step 402 of FIG. 14 termed "Agent extravasation". Thus, e.g. and referring to FIG. 1, it will be seen that the binding agent 105 is disposed at a first location within the device 10, and a chemical attractant 107 is disposed at a second location within the capture zone of device 10. Referring again to FIG. 14, in step 405 of the process, and in the embodiment depicted therein, if the binding of the biological target to the binding agent is nonreversible, then the biological target will accumulate in the capture zone. Referring to FIG. 13, this accumulation is defined as "Cell storage". The biological target may be removed from the capture zone either through an access port or through other means as depicted in step 404 of FIG. 14. The biological target may or may not be deprived of nutrients necessary to maintain cell vitality. Referring again to FIG. 14, as in the process of step 315 in FIG. 8*a* a portion of biological agents, which are unbound along with the bodily fluid and all other components within that fluid, can be returned to the venous blood supply in step 406. In one embodiment the device 10 described within the processes on page 15, will be removed from the arterial and venous attachments and flushed with the appropriate buffers for the removal of cells, cellular particles, cellular debris, fibrin and other large macromolecules typically found in circulating bodily fluids, which are bound to the luminal surface of one, two or the multiplicity, n chambers. In this embodiment the binding agents and any other required matrix materials which were removed during device function or flushing will be replaced at the appropriate spatial concentration. In another embodiment the device 10 can be replaced with a completely separate device where the original is disposed of.

Figure 15:
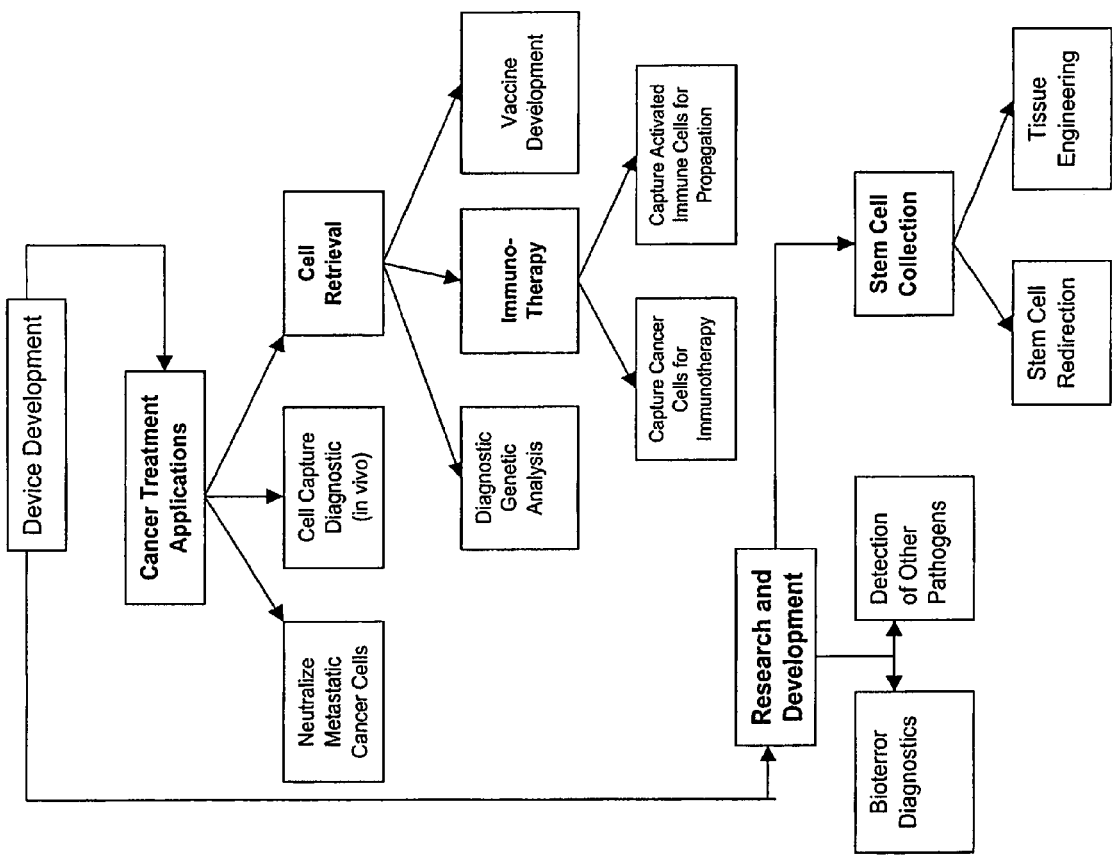
FIG. 15 is a diagram that illustrates multiple utilities of the instant invention.

The instant invention has a multitude of uses. FIG. 15 illustrates a small portion of these uses. The cell capture process may be utilized in the cancer treatment market as an adjuvant for the prevention of secondary tumor formation. It also fulfills an unmet need for metastatic treatment to kill cancer cells and provides continuous collection of metastatic cancer cells throughout the treatment of primary tumors. It also provides cellular detection of cancer cells and can be adapted to assist in immunotherapy. The process of the instant invention also has uses outside of the cancer treatment field. The process can collect HIV cells for use in finding effective cytotoxins. In another embodiment, immune cells can be collected for propagation and reuse in the patient and can also be utilized in the melanoma immunotherapy. The process also finds uses in basic research and development. The process may greatly facilitate the detection of pathogens, harvest the patient's own stem cells, and be a key component in tissue engineering. The uses outlined in FIG. 15 should be considered illustrative only, and are not intended to limit the application of the invention.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims. While the invention has been described with reference to certain embodiments, it will be understood by those skilled in the art that various changes may be made and equivalents may be substituted for elements thereof to adapt to particular situations without departing from the scope of the disclosure. Therefore, it is intended that the claims not be limited to the particular embodiments disclosed, but that the claims will include all embodiments falling within the scope and spirit of the appended claims.

What is claimed is:

1. A process for treating a stem cell comprising the steps of:
introducing a fluid that includes at least one stem cell to an inlet of an assembly, the assembly comprising a flow chamber with a cross-sectional dimension less than 150 microns for conveying the fluid through the assembly, the flow chamber having a capture zone comprising a stem cell-specific binding agent;
permitting the fluid to pass through the flow chamber wherein the stem cell undergoes flux rolling along the stem cell-specific binding agent.

2. A process for treating a stem cell in the blood of an organism comprising the steps of:
placing an assembly in fluid communication with a vein or artery of an organism, the assembly comprising a flow chamber with a cross-sectional dimension less than 150 microns for conveying a first portion of blood through the assembly, the flow chamber having a capture zone comprising a stem cell-specific binding agent;
permitting blood to pass through the flow chamber, wherein during flow of the blood through the flow chamber, the stem cell undergoes flux rolling along the stem cell-specific binding agent.

3. The process as recited in claim 2, wherein the stem cell-specific binding agent is a peptide or protein.

4. The process as recited in claim 2, wherein the stem cell-specific binding agent comprises E-selectin, P-selectin, ICAM-1, cadherin-11 or a combination thereof.

5. The process as recited in claim 2, wherein the assembly further comprises a bypass chamber for conveying a second portion of blood through the assembly without passing the second portion through the flow chamber.

6. The process as recited in claim 2, wherein the assembly comprises a stent, catheter, cannula, capsule, patch, wire, infusion sleeve, fiber, shunt or graft.

7. The process as recited in claim 2, wherein the assembly is formed from a natural or synthetic polymer, fiber, diatomaceous earth, glass, metal, colloid or plastic.

8. The process as recited in claim 2, wherein the stem cell-specific binding agent is immobilized to a surface of the capture zone.

9. The process as recited in claim 2, wherein the stem cell-specific binding agent is adsorbed or covalently bonded to a surface of the capture zone.

10. The process as recited in claim 2, wherein after flux rolling of the stem cell along the stem cell-specific binding agent, the stem cell is removed from the capture zone and collected.

11. The process as recited in claim 2, wherein the flow chamber includes an access port.

12. A process for treating a cancer cell in the blood of an organism comprising the steps of:
implanting an assembly in an organism such that the assembly is in fluid communication with a vein or artery of the organism, the assembly comprising a flow chamber with a cross-sectional dimension less than 150 microns for conveying a first portion of blood through the assembly, the flow chamber having a capture zone comprising a cancer cell-specific binding agent;
permitting blood to pass through the flow chamber, wherein during flow of the blood through the flow chamber, the cancer cell undergoes flux rolling along the cancer cell-specific binding agent.

13. The process as recited in claim 12, wherein the assembly further comprises a bypass chamber for conveying a second portion of blood through the assembly without passing the second portion through the flow chamber.

14. The process as recited in claim 12, wherein the capture zone further comprises an anti-proliferative agent that is adsorbed or covalently bonded to a surface of the capture zone.

15. The process as recited in claim 12, wherein the cancer cell-specific binding agent comprises E-selectin, P-selectin, ICAM-1, cadherin-11 or a combination thereof.

16. The process as recited in claim 12, further comprising a second assembly which is substantially identical to the first assembly, the first and second assemblies being in fluid communication such that the blood passes through each assembly in series.

* * * * *